US007825218B2

(12) United States Patent
Riggs et al.

(10) Patent No.: US 7,825,218 B2
(45) Date of Patent: Nov. 2, 2010

(54) SOLUBILIZATION AND PURIFICATION OF A TARGET PROTEIN FUSED TO A MUTANT MALTOSE-BINDING PROTEIN

(75) Inventors: Paul Riggs, Hooksett, NH (US);
Pei-Chung Hsieh, Topsfield, MA (US);
Iris Walker, Rowley, MA (US); Paul A. Colussi, Gloucester, MA (US); Mehul Ganatra, Gloucester, MA (US);
Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 72 days.

(21) Appl. No.: 12/297,105

(22) PCT Filed: Apr. 14, 2007

(86) PCT No.: PCT/US2007/009100

§ 371 (c)(1),
(2), (4) Date: Nov. 14, 2008

(87) PCT Pub. No.: WO2007/120809

PCT Pub. Date: Oct. 25, 2007

(65) Prior Publication Data

US 2009/0305342 A1    Dec. 10, 2009

Related U.S. Application Data

(60) Provisional application No. 60/792,133, filed on Apr. 14, 2006.

(51) Int. Cl.
*C07K 14/00* (2006.01)
*C07H 21/04* (2006.01)
*C12P 1/00* (2006.01)
*C12P 21/06* (2006.01)

(52) U.S. Cl. .............. 530/350; 435/69.1; 435/267; 536/23.1

(58) Field of Classification Search .............. None
See application file for complete search history.

(56) References Cited

FOREIGN PATENT DOCUMENTS

WO    2006023635    3/2006

OTHER PUBLICATIONS

Hennig, et al., Protein Expression and Purification, 14:367-370 (1998).
Kapust & Waugh, Protein Sci. 8:1668-74 (1999).

*Primary Examiner*—Nashaat T Nashed
(74) *Attorney, Agent, or Firm*—Harriet M. Strimpel

(57) ABSTRACT

Methods and compositions are provided for increasing at least one of: (i) binding affinity of a target protein for a maltodextrin substrate and/or (ii) solubility of a target protein. The methods and compositions relate to a modified maltose-binding protein.

7 Claims, 20 Drawing Sheets

Figure 2A-1 (SEQ ID NO:1 and 2)

```
1501 ---------+---------+---------+---------+---------+---------+  1560
     GCACTTCACCAACAAGGACCATAGCATATGAAAATCGAAGAAGGTAAACTGGTAATCTGG
                                   M  K  I  E  E  G  K  L  V  I  W

1561 ---------+---------+---------+---------+---------+---------+  1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D

1621 ---------+---------+---------+---------+---------+---------+  1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V

1681 ---------+---------+---------+---------+---------+---------+  1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y

1741 ---------+---------+---------+---------+---------+---------+  1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y

1801 ---------+---------+---------+---------+---------+---------+  1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V

1861 ---------+---------+---------+---------+---------+---------+  1920
     GAAGCGTTATCGCTGATTTATAACAAAGATCTGCTGCCGAACCCGCCAAAAAACCTGGGAA
      E  A  L  S  L  I  Y  N  K  D  L  L  P  N  P  P  K  T  W  E

1921 ---------+---------+---------+---------+---------+---------+  1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F  N

1981 ---------+---------+---------+---------+---------+---------+  2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F  K

2041 ---------+---------+---------+---------+---------+---------+  2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A

2101 ---------+---------+---------+---------+---------+---------+  2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ---------+---------+---------+---------+---------+---------+  2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ---------+---------+---------+---------+---------+---------+  2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ---------+---------+---------+---------+---------+---------+  2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S
```

Figure 2A-2

```
2341  ---------+---------+---------+---------+---------+---------+  2400
      CCGAACAAAGAGCTGGCAAAAGAGTTCCTCGAAAACTATCTGCTGACTGATGAAGGTCTG
       P  N  K  E  L  A  K  E  F  L  E  N  Y  L  L  T  D  E  G  L

2401  ---------+---------+---------+---------+---------+---------+  2460
      GAAGCGGTTAATAAAGACAAACCGCTGGGTGCCGTAGCGCTGAAGTCTTACGAGGAAGAG
       E  A  V  N  K  D  K  P  L  G  A  V  A  L  K  S  Y  E  E  E

2461  ---------+---------+---------+---------+---------+---------+  2520
      TTGGCGAAAGATCCACGTATTGCCGCCACTATGGAAAACGCCCAGAAAGGTGAAATCATG
       L  A  K  D  P  R  I  A  A  T  M  E  N  A  Q  K  G  E  I  M

2521  ---------+---------+---------+---------+---------+---------+  2580
      CCGAACATCCCGCAGATGTCCGCTTTCTGGTATGCCGTGCGTACTGCGGTGATCAACGCC
       P  N  I  P  Q  M  S  A  F  W  Y  A  V  R  T  A  V  I  N  A

2581  ---------+---------+---------+---------+---------+---------+  2640
      GCCAGCGGTCGTCAGACTGTCGATGAAGCCCTGAAAGACGCGCAGACTAATTCGAGCTCG
       A  S  G  R  Q  T  V  D  E  A  L  K  D  A  Q  T  N  S  S  S

2641  ---------+---------+---------+---------+--------             2688
      AACAACAACAACAATAACAATAACAACAACCTCGGGATCGAGGGAAGG
       N  N  N  N  N  N  N  N  N  L  G  I  E  G  R
```

Figure 2B-1 (SEQ ID NO:3 and 4)

```
1501  ----------+----------+----------+----------+----------+----------+  1560
      GCACTTCACCAACAAGGACCATAGCATATGAAAATCGAAGAAGGTAAACTGGTAATCTGG
                                      M  K  I  E  E  G  K  L  V  I  W

1561  ----------+----------+----------+----------+----------+----------+  1620
      ATTAACGGCGATAAAGGCTATAGCGGTCTCGCTGAAGTCGGTAAGAAATTCGAGAAAGAT
       I  N  G  D  K  G  Y  S  G  L  A  E  V  G  K  K  F  E  K  D

1621  ----------+----------+----------+----------+----------+----------+  1680
      ACCGGAATTAAAGTCACCGTTGAGCATCCGGATAAACTGGAAGAGAAATTCCCACAGGTT
       T  G  I  K  V  T  V  E  H  P  D  K  L  E  E  K  F  P  Q  V

1681  ----------+----------+----------+----------+----------+----------+  1740
      GCGGCAACTGGCGATGGCCCTGACATTATCTTCTGGGCACACGACCGCTTTGGTGGCTAC
       A  A  T  G  D  G  P  D  I  I  F  W  A  H  D  R  F  G  G  Y

1741  ----------+----------+----------+----------+----------+----------+  1800
      GCTCAATCTGGCCTGTTGGCTGAAATCACCCCGGACAAAGCGTTCCAGGACAAGCTGTAT
       A  Q  S  G  L  L  A  E  I  T  P  D  K  A  F  Q  D  K  L  Y

1801  ----------+----------+----------+----------+----------+----------+  1860
      CCGTTTACCTGGGATGCCGTACGTTACAACGGCAAGCTGATTGCTTACCCGATCGCTGTT
       P  F  T  W  D  A  V  R  Y  N  G  K  L  I  A  Y  P  I  A  V

1861  ----------+----------+----------+----------+----------+----------+  1920
      GAAGCGTTATCGCTGATTTATAACAAAGATCTGCTGCCGAACCCGCCAAAAACCTGGGAA
       E  A  L  S  L  I  Y  N  K  D  L  L  P  N  P  P  K  T  W  E

1921  ----------+----------+----------+----------+----------+----------+  1980
      GAGATCCCGGCGCTGGATAAAGAACTGAAAGCGAAAGGTAAGAGCGCGCTGATGTTCAAC
       E  I  P  A  L  D  K  E  L  K  A  K  G  K  S  A  L  M  F  N

1981  ----------+----------+----------+----------+----------+----------+  2040
      CTGCAAGAACCGTACTTCACCTGGCCGCTGATTGCTGCTGACGGGGGTTATGCGTTCAAG
       L  Q  E  P  Y  F  T  W  P  L  I  A  A  D  G  G  Y  A  F  K

2041  ----------+----------+----------+----------+----------+----------+  2100
      TATGAAAACGGCAAGTACGACATTAAAGACGTGGGCGTGGATAACGCTGGCGCGAAAGCG
       Y  E  N  G  K  Y  D  I  K  D  V  G  V  D  N  A  G  A  K  A

2101  ----------+----------+----------+----------+----------+----------+  2160
      GGTCTGACCTTCCTGGTTGACCTGATTAAGAACAAACACATGAATGCAGACACCGATTAC
       G  L  T  F  L  V  D  L  I  K  N  K  H  M  N  A  D  T  D  Y

2161  ----------+----------+----------+----------+----------+----------+  2220
      TCCATCGCAGAAGCTGCCTTTAATAAAGGCGAAACAGCGATGACCATCAACGGCCCGTGG
       S  I  A  E  A  A  F  N  K  G  E  T  A  M  T  I  N  G  P  W

2221  ----------+----------+----------+----------+----------+----------+  2280
      GCATGGTCCAACATCGACACCAGCAAAGTGAATTATGGTGTAACGGTACTGCCGACCTTC
       A  W  S  N  I  D  T  S  K  V  N  Y  G  V  T  V  L  P  T  F

2281  ----------+----------+----------+----------+----------+----------+  2340
      AAGGGTCAACCATCCAAACCGTTCGTTGGCGTGCTGAGCGCAGGTATTAACGCCGCCAGT
       K  G  Q  P  S  K  P  F  V  G  V  L  S  A  G  I  N  A  A  S
```

Figure 2B-2

```
2341 ---------+---------+---------+---------+---------+---------+ 2400
     CCGAACAAAGAGCTGGCAAAAGAGTTCCTCGAAAACTATCTGCTGACTGATGAAGGTCTG
     P  N  K  E  L  A  K  E  F  L  E  N  Y  L  L  T  D  E  G  L

2401 ---------+---------+---------+---------+---------+---------+ 2460
     GAAGCGGTTAATAAAGACGAACCGCTGGGTGCCGTAGCGCTGAAGTCTTACGAGGAAGAG
     E  A  V  N  K  D  E  P  L  G  A  V  A  L  K  S  Y  E  E  E

2461 ---------+---------+---------+---------+---------+---------+ 2520
     TTGGTGAAAGATCCACGTATTGCCGCCACTATGGAAAACGCCCAGAAAGGTGAAATCATG
     L  V  K  D  P  R  I  A  A  T  M  E  N  A  Q  K  G  E  I  M

2521 ---------+---------+---------+---------+---------+---------+ 2580
     CCGAACATCCCGCAGATGTCCGCTTTCTGGTATGCCGTGCGTACTGCGGTGATCAACGCC
     P  N  I  P  Q  M  S  A  F  W  Y  A  V  R  T  A  V  I  N  A

2581 ---------+---------+---------+---------+---------+---------+ 2640
     GCCAGCGGTCGTCAGACTGTCGATGAAGCCCTGAAAGACGCGCAGACTAATTCGAGCTCG
     A  S  G  R  Q  T  V  D  E  A  L  K  D  A  Q  T  N  S  S  S

2641 ---------+---------+---------+---------+-------- 2688
     AACAACAACAACAATAACAATAACAACAACCTCGGGATCGAGGGAAGG
     N  N  N  N  N  N  N  N  N  L  G  I  E  G  R
```

Figure 2C-1 (SEQ ID NO:5 and 6)

```
1501   ---------+---------+---------+---------+---------+---------+   1560
       GCACTTCACCAACAAGGACCATAGCATATGAAAATCGAAGAAGGTAAACTGGTAATCTGG
                                    M  K  I  E  E  G  K  L  V  I  W

1561   ---------+---------+---------+---------+---------+---------+   1620
       ATTAACGGCGATAAAGGCTATAACGGTCTCGCTGAAGTCGGTAAGAAATTCGAGAAAGAT
        I  N  G  D  K  G  Y  N  G  L  A  E  V  G  K  K  F  E  K  D

1621   ---------+---------+---------+---------+---------+---------+   1680
       ACCGGAATTAAAGTCACCGTTGAGCATCCGGATAAACTGGAAGAGAAATTCCCACAGGTT
        T  G  I  K  V  T  V  E  H  P  D  K  L  E  E  K  F  P  Q  V

1681   ---------+---------+---------+---------+---------+---------+   1740
       GCGGCAACTGGCGATGCCCTGACATTATCTTCTGGGCACACGACCGCTTTGGTGGCTAC
        A  A  T  G  D  G  P  D  I  I  F  W  A  H  D  R  F  G  G  Y

1741   ---------+---------+---------+---------+---------+---------+   1800
       GCTCAATCTGGCCTGTTGGCTGAAATCACCCCGGACAAAGCGTTCCAGGACAAGCTGTAT
        A  Q  S  G  L  L  A  E  I  T  P  D  K  A  F  Q  D  K  L  Y

1801   ---------+---------+---------+---------+---------+---------+   1860
       CCGTTTACCTGGGATGCCGTACGTTACAACGGCAAGCTGATTGCTTACCCGATCGCTGTT
        P  F  T  W  D  A  V  R  Y  N  G  K  L  I  A  Y  P  I  A  V

1861   ---------+---------+---------+---------+---------+---------+   1920
       GAAGCGTTATCGCTGATTTATAACAAAGATCTGCTGCCGAACCCGCCAAAAACCTGGGAA
        E  A  L  S  L  I  Y  N  K  D  L  L  P  N  P  P  K  T  W  E

1921   ---------+---------+---------+---------+---------+---------+   1980
       GAGATCCCGGCGCTGGATAAAGAACTGAAAGCGAAAGGTAAGACCGCGCTGATGTTCAAC
        E  I  P  A  L  D  K  E  L  K  A  K  G  K  T  A  L  M  F  N

1981   ---------+---------+---------+---------+---------+---------+   2040
       CTGCAAGAACCGTACTTCACCTGGCCGCTGATTGCTGCTGACGGGGGCTATGCGTTCAAG
        L  Q  E  P  Y  F  T  W  P  L  I  A  A  D  G  G  Y  A  F  K

2041   ---------+---------+---------+---------+---------+---------+   2100
       TATGAAAACGGCAAGTACGACATTAAAGACGTGGGCGTGGATAACGCTGGCGCGAAAGCG
        Y  E  N  G  K  Y  D  I  K  D  V  G  V  D  N  A  G  A  K  A

2101   ---------+---------+---------+---------+---------+---------+   2160
       GGTCTGACCTTCCTGGTTGACCTGATTAAAAACAAACACATGAATGCAGACACCGATTAC
        G  L  T  F  L  V  D  L  I  K  N  K  H  M  N  A  D  T  D  Y

2161   ---------+---------+---------+---------+---------+---------+   2220
       TCCATCGCAGAAGCTGCCTTTAATAAAGGCGAAACAGCGATGACCATCAACGGCCCGTGG
        S  I  A  E  A  A  F  N  K  G  E  T  A  M  T  I  N  G  P  W

2221   ---------+---------+---------+---------+---------+---------+   2280
       GCATGGTCCAACATCGACACCAGCAAAGTGAATTATGGTGTAACGGTACTGCCGACCTTC
        A  W  S  N  I  D  T  S  K  V  N  Y  G  V  T  V  L  P  T  F

2281   ---------+---------+---------+---------+---------+---------+   2340
       AAGGGTCAACCATCCAAACCGTTCGTTGGCGTGCTGAGCGCAGGTATTAACGCCGCCAGT
        K  G  Q  P  S  K  P  F  V  G  V  L  S  A  G  I  N  A  A  S
```

Figure 2C-2

```
2341    ---------+---------+---------+---------+---------+---------+    2400
        CCGAACAAAGAGCTGGCAAAAGAGTTCCTCGAAAACTATCTGCTGACTGATGAAGGTCTG
         P  N  K  E  L  A  K  E  F  L  E  N  Y  L  L  T  D  E  G  L

2401    ---------+---------+---------+---------+---------+---------+    2460
        GAAGCGGTTAATAAAGACAAACCGCTGGGTGCCGTAGCGCTGAAGTCTTACGAGGAAGAG
         E  A  V  N  K  D  K  P  L  G  A  V  A  L  K  S  Y  E  E  E

2461    ---------+---------+---------+---------+---------+---------+    2520
        TTGGCGAAAGATCCACGTATTGCCGCCACTATGGAAAACGCCCAGAAAGGTGAAATCATG
         L  A  K  D  P  R  I  A  A  T  M  E  N  A  Q  K  G  E  I  M

2521    ---------+---------+---------+---------+---------+---------+    2580
        CCGAACATCCCGCAGATGTCCGCTTTCTGGTATGCCGTGCGTACTGCGGTGATCAACGCC
         P  N  I  P  Q  M  S  A  F  W  Y  A  V  R  T  A  V  I  N  A

2581    ---------+---------+---------+---------+---------+---------+    2640
        GCCAGCGGTCGTCAGACTGTCGATGAAGCCCTGAAAGACGCGCAGACTAATTCGAGCTCG
         A  S  G  R  Q  T  V  D  E  A  L  K  D  A  Q  T  N  S  S  S

2641    ---------+---------+---------+---------+--------                 2688
        AACAACAACAACAATAACAATAACAACAACCTCGGGATCGAGGGAAGG
         N  N  N  N  N  N  N  N  N  L  G  I  E  G  R
```

Figure 5-1 (SEQ ID NO:7)

```
   1   CCGACACCAT CGAATGGTGC AAAACCTTTC GCGGTATGGC ATGATAGCGC
  51   CCGGAAGAGA GTCAATTCAG GGTGGTGAAT GTGAAACCAG TAACGTTATA
 101   CGATGTCGCA GAGTATGCCG GTGTCTCTTA TCAGACCGTT TCCCGCGTGG
 151   TGAACCAGGC CAGCCACGTT TCTGCGAAAA CGCGGGAAAA AGTGGAAGCG
 201   GCGATGGCGG AGCTGAATTA CATTCCCAAC CGCGTGGCAC AACAACTGGC
 251   GGGCAAACAG TCGTTGCTGA TTGGCGTTGC CACCTCCAGT CTGGCCCTGC
 301   ACGCGCCGTC GCAAATTGTC GCGGCGATTA AATCTCGCGC CGATCAACTG
 351   GGTGCCAGCG TGGTGGTGTC GATGGTAGAA CGAAGCGGCG TCGAAGCCTG
 401   TAAAGCGGCG GTGCACAATC TTCTCGCGCA ACGCGTCAGT GGGCTGATCA
 451   TTAACTATCC GCTGGATGAC CAGGATGCCA TTGCTGTGGA AGCTGCCTGC
 501   ACTAATGTTC CGGCGTTATT TCTTGATGTC TCTGACCAGA CACCCATCAA
 551   CAGTATTATT TTCTCCCATG AAGACGGTAC GCGACTGGGC GTGGAGCATC
 601   TGGTCGCATT GGGTCACCAG CAAATCGCGC TGTTAGCGGG CCCATTAAGT
 651   TCTGTCTCGG CGCGTCTGCG TCTGGCTGGC TGGCATAAAT ATCTCACTCG
 701   CAATCAAATT CAGCCGATAG CGGAACGGGA AGGCGACTGG AGTGCCATGT
 751   CCGGTTTTCA ACAAACCATG CAAATGCTGA ATGAGGGCAT CGTTCCCACT
 801   GCGATGCTGG TTGCCAACGA TCAGATGGCG CTGGGCGCAA TGCGCGCCAT
 851   TACCGAGTCC GGGCTGCGCG TTGGTGCGGA TATCTCGGTA GTGGGATACG
 901   ACGATACCGA AGACAGCTCA TGTTATATCC CGCCGTTAAC CACCATCAAA
 951   CAGGATTTTC GCCTGCTGGG GCAAACCAGC GTGGACCGCT TGCTGCAACT
1001   CTCTCAGGGC CAGGCGGTGA AGGGCAATCA GCTGTTGCCC GTCTCACTGG
1051   TGAAAAGAAA AACCACCCTG GCGCCCAATA CGCAAACCGC CTCTCCCCGC
1101   GCGTTGGCCG ATTCATTAAT GCAGCTGGCA CGACAGGTTT CCCGACTGGA
1151   AAGCGGGCAG TGAGCGCAAC GCAATTAATG TGAGTTAGCT CACTCATTAG
1201   GCACAATTCT CATGTTTGAC AGCTTATCAT CGACTGCACG GTGCACCAAT
1251   GCTTCTGGCG TCAGGCAGCC ATCGGAAGCT GTGGTATGGC TGTGCAGGTC
1301   GTAAATCACT GCATAATTCG TGTCGCTCAA GGCGCACTCC CGTTCTGGAT
1351   AATGTTTTTT GCGCCGACAT CATAACGGTT CTGGCAAATA TTCTGAAATG
```

Figure 5-2

```
1401  AGCTGTTGAC AATTAATCAT CGGCTCGTAT AATGTGTGGA ATTGTGAGCG
1451  GATAACAATT TCACACAGGA AACAGCCAGT CCGTTTAGGT GTTTTCACGA
1501  GCACTTCACC AACAAGGACC ATAGATTATG AAAATCGAAG AAGGTAAACT
1551  GGTAATCTGG ATTAACGGCG ATAAAGGCTA TAACGGTCTC GCTGAAGTCG
1601  GTAAGAAATT CGAGAAAGAT ACCGGAATTA AAGTCACCGT TGAGCATCCG
1651  GATAAACTGG AAGAGAAATT CCCACAGGTT GCGGCAACTG GCGATGGCCC
1701  TGACATTATC TTCTGGGCAC ACGACCGCTT TGGTGGCTAC GCTCAATCTG
1751  GCCTGTTGGC TGAAATCACC CCGGACAAAG CGTTCCAGGA CAAGCTGTAT
1801  CCGTTTACCT GGGATGCCGT ACGTTACAAC GGCAAGCTGA TTGCTTACCC
1851  GATCGCTGTT GAAGCGTTAT CGCTGATTTA TAACAAAGAT CTGCTGCCGA
1901  ACCCGCCAAA AACCTGGGAA GAGATCCCGG CGCTGGATAA AGAACTGAAA
1951  GCGAAAGGTA AGAGCGCGCT GATGTTCAAC CTGCAAGAAC CGTACTTCAC
2001  CTGGCCGCTG ATTGCTGCTG ACGGGGGTTA TGCGTTCAAG TATGAAAACG
2051  GCAAGTACGA CATTAAAGAC GTGGGCGTGG ATAACGCTGG CGCGAAAGCG
2101  GGTCTGACCT TCCTGGTTGA CCTGATTAAA AACAAACACA TGAATGCAGA
2151  CACCGATTAC TCCATCGCAG AAGCTGCCTT TAATAAAGGC GAAACAGCGA
2201  TGACCATCAA CGGCCCGTGG GCATGGTCCA ACATCGACAC CAGCAAAGTG
2251  AATTATGGTG TAACGGTACT GCCGACCTTC AAGGGTCAAC CATCCAAACC
2301  GTTCGTTGGC GTGCTGAGCG CAGGTATTAA CGCCGCCAGT CCGAACAAAG
2351  AGCTGGCAAA AGAGTTCCTC GAAAACTATC TGCTGACTGA TGAAGGTCTG
2401  GAAGCGGTTA ATAAAGACAA ACCGCTGGGT GCCGTAGCGC TGAAGTCTTA
2451  CGAGGAAGAG TTGGCGAAAG ATCCACGTAT TGCCGCCACC ATGGAAAACG
2501  CCCAGAAAGG TGAAATCATG CCGAACATCC CGCAGATGTC CGCTTTCTGG
2551  TATGCCGTGC GTACTGCGGT GATCAACGCC GCCAGCGGTC GTCAGACTGT
2601  CGATGAAGCC CTGAAAGACG CGCAGACTAA TTCGAGCTCG AACAACAACA
2651  ACAATAACAA TAACAACAAC CTCGGGATCG AGGGAAGGGG TACGCTCGAG
2701  GGTTCTCAGC ATGCACCGGG TGGCCTGACC GGTCTGAACT CAGGCCTCAC
2751  GACAAATCCT GGTGTATCCG CTTGGCAGGT CAACACAGCT TATACTGCGG
```

Figure 5-3

```
2801  GACAATTGGT CACATATAAC GGCAAGACGT ATAAATGTTT GCAGCCCCAC
2851  ACCTCCTTGG CAGGATGGGA ACCATCCAAC GTTCCTGCCT TGTGGCAGCT
2901  TCAATGACTG CAGGCAAGCT TGGCACTGGC CGTCGTTTTA CAACGTCGTG
2951  ACTGGGAAAA CCCTGGCGTT ACCCAACTTA ATCGCCTTGC AGCACATCCC
3001  CCTTTCGCCA GCTGGCGTAA TAGCGAAGAG GCCCGCACCG ATCGCCCTTC
3051  CCAACAGTTG CGCAGCCTGA ATGGCGAATG GCAGCTTGGC TGTTTTGGCG
3101  GATGAGATAA GATTTTCAGC CTGATACAGA TTAAATCAGA ACGCAGAAGC
3151  GGTCTGATAA AACAGAATTT GCCTGGCGGC AGTAGCGCGG TGGTCCCACC
3201  TGACCCCATG CCGAACTCAG AAGTGAAACG CCGTAGCGCC GATGGTAGTG
3251  TGGGGTCTCC CCATGCGAGA GTAGGGAACT GCCAGGCATC AAATAAAACG
3301  AAAGGCTCAG TCGAAAGACT GGGCCTTTCG TTTTATCTGT TGTTTGTCGG
3351  TGAACGCTCT CCTGAGTAGG ACAAATCCGC CGGGAGCGGA TTTGAACGTT
3401  GCGAAGCAAC GGCCCGGAGG GTGGCGGGCA GGACGCCCGC CATAAACTGC
3451  CAGGCATCAA ATTAAGCAGA AGGCCATCCT GACGGATGGC CTTTTTGCGT
3501  TTCTACAAAC TCTTTTTGTT TATTTTTCTA AATACATTCA AATATGTATC
3551  CGCTCATGAG ACAATAACCC TGATAAATGC TTCAATAATA TTGAAAAAGG
3601  AAGAGTATGA GTATTCAACA TTTCCGTGTC GCCCTTATTC CCTTTTTTGC
3651  GGCATTTTGC CTTCCTGTTT TTGCTCACCC AGAAACGCTG GTGAAAGTAA
3701  AAGATGCTGA AGATCAGTTG GGTGCACGAG TGGGTTACAT CGAACTGGAT
3751  CTCAACAGCG GTAAGATCCT TGAGAGTTTT CGCCCCGAAG AACGTTCTCC
3801  AATGATGAGC ACTTTTAAAG TTCTGCTATG TGGCGCGGTA TTATCCCGTG
3851  TTGACGCCGG GCAAGAGCAA CTCGGTCGCC GCATACACTA TTCTCAGAAT
3901  GACTTGGTTG AGTACTCACC AGTCACAGAA AAGCATCTTA CGGATGGCAT
3951  GACAGTAAGA GAATTATGCA GTGCTGCCAT AACCATGAGT GATAACACTG
4001  CGGCCAACTT ACTTCTGACA ACGATCGGAG GACCGAAGGA GCTAACCGCT
4051  TTTTTGCACA ACATGGGGGA TCATGTAACT CGCCTTGATC GTTGGGAACC
4101  GGAGCTGAAT GAAGCCATAC CAAACGACGA GCGTGACACC ACGATGCCTG
4151  TAGCAATGGC AACAACGTTG CGCAAACTAT TAACTGGCGA ACTACTTACT
```

Figure 5-4

```
4201 CTAGCTTCCC GGCAACAATT AATAGACTGG ATGGAGGCGG ATAAAGTTGC
4251 AGGACCACTT CTGCGCTCGG CCCTTCCGGC TGGCTGGTTT ATTGCTGATA
4301 AATCTGGAGC CGGTGAGCGT GGGTCTCGCG GTATCATTGC AGCACTGGGG
4351 CCAGATGGTA AGCCCTCCCG TATCGTAGTT ATCTACACGA CGGGGAGTCA
4401 GGCAACTATG GATGAACGAA ATAGACAGAT CGCTGAGATA GGTGCCTCAC
4451 TGATTAAGCA TTGGTAACTG TCAGACCAAG TTTACTCATA TATACTTTAG
4501 ATTGATTTAC CCCGGTTGAT AATCAGAAAA GCCCCAAAAA CAGGAAGATT
4551 GTATAAGCAA ATATTTAAAT TGTAAACGTT AATATTTGT TAAAATTCGC
4601 GTTAAATTTT TGTTAAATCA GCTCATTTTT TAACCAATAG GCCGAAATCG
4651 GCAAAATCCC TTATAAATCA AAAGAATAGC CCGAGATAGG GTTGAGTGTT
4701 GTTCCAGTTT GGAACAAGAG TCCACTATTA AGAACGTGG ACTCCAACGT
4751 CAAAGGGCGA AAAACCGTCT ATCAGGGCGA TGGCCCACTA CGTGAACCAT
4801 CACCCAAATC AAGTTTTTTG GGGTCGAGGT GCCGTAAAGC ACTAAATCGG
4851 AACCCTAAAG GGAGCCCCCG ATTTAGAGCT TGACGGGGAA AGCCGGCGAA
4901 CGTGGCGAGA AAGGAAGGGA AGAAAGCGAA AGGAGCGGGC GCTAGGGCGC
4951 TGGCAAGTGT AGCGGTCACG CTGCGCGTAA CCACCACACC CGCCGCGCTT
5001 AATGCCGCC TACAGGGCGC GTAAAAGGAT CTAGGTGAAG ATCCTTTTTG
5051 ATAATCTCAT GACCAAAATC CCTTAACGTG AGTTTTCGTT CCACTGAGCG
5101 TCAGACCCCG TAGAAAAGAT CAAAGGATCT TCTTGAGATC CTTTTTTTCT
5151 GCGCGTAATC TGCTGCTTGC AAACAAAAAA ACCACCGCTA CCAGCGGTGG
5201 TTTGTTTGCC GGATCAAGAG CTACCAACTC TTTTTCCGAA GGTAACTGGC
5251 TTCAGCAGAG CGCAGATACC AAATACTGTC CTTCTAGTGT AGCCGTAGTT
5301 AGGCCACCAC TTCAAGAACT CTGTAGCACC GCCTACATAC CTCGCTCTGC
5351 TAATCCTGTT ACCAGTGGCT GCTGCCAGTG GCGATAAGTC GTGTCTTACC
5401 GGGTTGGACT CAAGACGATA GTTACCGGAT AAGGCGCAGC GGTCGGGCTG
5451 AACGGGGGGT TCGTGCACAC AGCCCAGCTT GGAGCGAACG ACCTACACCG
5501 AACTGAGATA CCTACAGCGT GAGCTATGAG AAAGCGCCAC GCTTCCCGAA
5551 GGGAGAAAGG CGGACAGGTA TCCGGTAAGC GGCAGGGTCG GAACAGGAGA
```

Figure 5-5

```
5601  GCGCACGAGG GAGCTTCCAG GGGGAAACGC CTGGTATCTT TATAGTCCTG
5651  TCGGGTTTCG CCACCTCTGA CTTGAGCGTC GATTTTTGTG ATGCTCGTCA
5701  GGGGGGCGGA GCCTATGGAA AAACGCCAGC AACGCGGCCT TTTTACGGTT
5751  CCTGGCCTTT TGCTGGCCTT TTGCTCACAT GTTCTTTCCT GCGTTATCCC
5801  CTGATTCTGT GGATAACCGT ATTACCGCCT TTGAGTGAGC TGATACCGCT
5851  CGCCGCAGCC GAACGACCGA GCGCAGCGAG TCAGTGAGCG AGGAAGCGGA
5901  AGAGCGCCTG ATGCGGTATT TTCTCCTTAC GCATCTGTGC GGTATTTCAC
5951  ACCGCATATG GTGCACTCTC AGTACAATCT GCTCTGATGC CGCATAGTTA
6001  AGCCAGTATA CACTCCGCTA TCGCTACGTG ACTGGGTCAT GGCTGCGCCC
6051  CGACACCCGC CAACACCCGC TGACGCGCCC TGACGGGCTT GTCTGCTCCC
6101  GGCATCCGCT TACAGACAAG CTGTGACCGT CTCCGGGAGC TGCATGTGTC
6151  AGAGGTTTTC ACCGTCATCA CCGAAACGCG CGAGGCAGCT GCGGTAAAGC
6201  TCATCAGCGT GGTCGTGCAG CGATTCACAG ATGTCTGCCT GTTCATCCGC
6251  GTCCAGCTCG TTGAGTTTCT CCAGAAGCGT TAATGTCTGG CTTCTGATAA
6301  AGCGGGCCAT GTTAAGGGCG GTTTTTTCCT GTTTGGTCAC TTGATGCCTC
6351  CGTGTAAGGG GGAATTTCTG TTCATGGGGG TAATGATACC GATGAAACGA
6401  GAGAGGATGC TCACGATACG GGTTACTGAT GATGAACATG CCCGGTTACT
6451  GGAACGTTGT GAGGGTAAAC AACTGGCGGT ATGGATGCGG CGGGACCAGA
6501  GAAAAATCAC TCAGGGTCAA TGCCAGCGCT TCGTTAATAC AGATGTAGGT
6551  GTTCCACAGG GTAGCCAGCA GCATCCTGCG ATGCAGATCC GGAACATAAT
6601  GGTGCAGGGC GCTGACTTCC GCGTTTCCAG ACTTTACGAA ACACGGAAAC
6651  CGAAGACCAT TCATGTTGTT GCTCAGGTCG CAGACGTTTT GCAGCAGCAG
6701  TCGCTTCACG TTCGCTCGCG TATCGGTGAT TCATTCTGCT AACCAGTAAG
6751  GCAACCCCGC CAGCCTAGCC GGGTCCTCAA CGACAGGAGC ACGATCATGC
6801  GCACCCGTGG CCAGGACCCA ACGCTGCCCG AAATT
```

Figure 7-1 (SEQ ID NO:8)

```
   1 AAGCTTGCCA CCATGAAAAT CGAAGAAGGT AAACTGGTAA TCTGGATTAA CGGCGATAAA
  61 GGCTATAACG GTCTCGCTGA AGTCGGTAAG AAATTCGAGA AGATACCGG AATTAAAGTC
 121 ACCGTTGAGC ATCCGGATAA ACTGGAAGAG AAATTCCCAC AGGTTGCGGC AACTGGCGAT
 181 GGCCCTGACA TTATCTTCTG GGCACACGAC CGCTTTGGTG GCTACGCTCA ATCTGGCCTG
 241 TTGGCTGAAA TCACCCCGGA CAAAGCGTTC CAGGACAAGC TGTATCCGTT TACCTGGGAT
 301 GCCGTACGTT ACAACGGCAA GCTGATTGCT TACCCGATCG CTGTTGAAGC GTTATCGCTG
 361 ATTTATAACA AAGATCTGCT GCCGAACCCG CCAAAAACCT GGGAAGAGAT CCCGGCGCTG
 421 GATAAAGAAC TGAAAGCGAA AGGTAAGAGC GCGCTGATGT TCAACCTGCA AGAACCGTAC
 481 TTCACCTGGC CGCTGATTGC TGCTGACGGG GGTTATGCGT TCAAGTATGA AAACGGCAAG
 541 TACGACATTA AAGACGTGGG CGTGGATAAC GCTGGCGCGA AAGCGGGTCT GACCTTCCTG
 601 GTTGACCTGA TTAAAAACAA ACACATGAAT GCAGACACCG ATTACTCCAT CGCAGAAGCT
 661 GCCTTTAATA AAGGCGAAAC AGCGATGACC ATCAACGGCC CGTGGGCATG GTCCAACATC
 721 GACACCAGCA AAGTGAATTA TGGTGTAACG GTACTGCCGA CCTTCAAGGG TCAACCATCC
 781 AAACCGTTCG TTGGCGTGCT GAGCGCAGGT ATTAACGCCG CCAGTCCGAA CAAAGAGCTG
 841 GCAAAAGAGT TCCTCGAAAA CTATCTGCTG ACTGATGAAG GTCTGGAAGC GGTTAATAAA
 901 GACAAACCGC TGGGTGCCGT AGCGCTGAAG TCTTACGAGG AAGAGTTGGT GAAAGATCCA
 961 CGTATTGCCG CCACTATGGA AAACGCCCAG AAAGGTGAAA TCATGCCGAA CATCCCGCAG
1021 ATGTCCGCTT TCTGGTATGC CGTGCGTACT GCGGTGATCA ACGCCGCCAG CGGTCGTCAG
1081 ACTGTCGATG AAGCCCTGAA AGACGCGCAG ACTAATTCGA GCTCGGATGA CGATGACAAG
1141 CTCGAGAATT CCGCATTCGG TAGTATGTCG GTTGCCGATT TGGAAGTTT AACTCGCTTG
1201 GAGGACAAGA TTCGTCTACT GCAAGAAGAT CTCGAATCCG AACGTGAACT TCGAAATAGA
1261 ATCGAACGAG AAAGAGCTGA TCTTAGTGTA CAACTGATTG CATTAACTGA TAGACTTGAA
1321 GATGCTGAGG GTACTACTGA TAGTCAGATT GAATCAAATC GTAAACGTGA AGCAGAATTG
1381 CAAAAATTAC GTAAATTATT GGAAGAATCA CAATTAGAAA ATGAAGATGC AATGAATGTT
1441 TTACGTAAAA AGCATCAAGA TGCATGTCTC GATTACGCTG AACAAATTGA ACAATTACAA
1501 AAGAAAAATT CAAAGATTGA TCGTGAACGT CAACGTCTGC AACATGAAGT AATTGAGCTT
1561 ACTGCGACAA TTGATCAACT TCAAAAGGAT AAGCATTTGG CGGAAAAAGC AGCGGAACGT
1621 TTTGAAGCGC AAACTATCGA ATTGAGTAAT AAAGTTGAAG ATTTAAATCG ACATGTTAAT
1681 GATTTAGCTC AACAACGTCA ACGTTTACAA GCTGAAAATA ACGATCTTCT CAAAGAGATT
1741 CATGATCAAA AAGTACAATT GGATAATTTG CAACACGTGA ATATCAACT TGCGCAACAA
1801 CTTGAAGAAG CACGTCGACC TGCAGGCAAG CTTGGCACTG GCCGTCGTTT TACAACGTCG
1861 TGAGCGGCCG CTTAATTAAG GCCTTGAATC GAGAATTTAT ACTTAGATAA GTATGTACTT
1921 ACAGGTATAT TTCTATGAGA TACTGATGTA TACATGCATG ATAATATTTA AACGGTTATT
1981 AGTGCCGATT GTCTTGTGCG ATAATGACGT TCCTATCAAA GCAATACACT TACCACCTAT
2041 TACATGGGCC AAGAAAATAT TTTCGAACTT GTTTAGAATA TTAGCACAGA GTATATGATG
2101 ATATCCGTTA GATTATGCAT GATTCATTCC TACAACTTTT TCGTAGCATA AGGATTAATT
2161 ACTTGGATGC CAATAAAAAA AAAAAACATC GAGAAATTT CAGCATGCTC AGAAACAATT
2221 GCAGTGTATC AAAGTAAAAA AAAGATTTTC ACTACATGTT CCTTTTGAAG AAAGAAAATC
2281 ATGGAACATT AGATTTACAA AAATTTAACC ACCGCTGATT AACGATTAGA CCGTTAAGCG
2341 CACAACAGGT TATTAGTACA GAGAAAGCAT TCTGTGGTGT TGCCCCGGAC TTTCTTTTGC
2401 GACATAGGTA AATCGAATAC CATCATACTA TCTTTTCCAA TGACTCCCTA AGAAAGACT
2461 CTTCTTCGAT GTTGTATACG TTGGAGCATA GGGCAAGAAT TGTGGCTTGA GATCATCCTT
2521 TTGTTGTTTC CGGGTGTACA ATATGGACTT CCTCTTTTCT GGCAACCAAA CCCATACATC
2581 GGGATTCCTA TAATACCTTC GTTGGTCTCC CTAACATGTA GGTGGCGGAG GGAGATATA
2641 CAATAGAACA GATACCAGAC AAGACATAAT GGGCTAAACA AGACTACACC AATTACACTG
2701 CCTCATTGAT GGTGGTACAT AACGAACTAA TACTGTAGCC CTAGACTTGA TAGCCATCAT
2761 CATATCGAAG TTTCACTACC CTTTTCCAT TTGCCATCTA TTGAAGTAAT AATAGGCGCA
2821 TGCAACTTCT TTTCTTTTTT TTTCTTTTCT CTCTCCCCCG TTGTTGTCTC ACCATATCCG
2881 CAATGACAAA AAAATGATGG AAGACACTAA AGGAAAAAAT TAACGACAAA GACAGCACCA
2941 ACAGATGTCG TTGTTCCAGA GCTGATGAGG GGTATCTCGA AGCACACGAA ACTTTTTCCT
3001 TCCTTCATTC ACGCACACTA CTCTCTAATG AGCAACGGTA TACGGCCTTC CTTCCAGTTA
```

Figure 7-2

```
3061 CTTGAATTTG AAATAAAAAA AAGTTTGCTG TCTTGCTATC AAGTATAAAT AGACCTGCAA
3121 TTATTAATCT TTTGTTTCCT CGTCATTGTT CTCGTTCCCT TTCTTCCTTG TTTCTTTTTC
3181 TGCACAATAT TTCAAGCTAT ACCAAGCATA CAATCAAGGA ATTCCGGATC CGCCACCATG
3241 CCTCAATCCT GGGAAGAACT GGCCGCTGAT AAGCGCGCCC GCCTCGCAAA AACCATCCCT
3301 GATGAATGGA AAGTCCAGAC GCTGCCTGCG GAAGACAGCG TTATTGATTT CCCAAAGAAA
3361 TCGGGGATCC TTTCAGAGGC CGAACTGAAG ATCACAGAGG CTTCCGCTGC GGATCTTGTG
3421 TCCAAGCTGG CGGCCGGAGA GTTGACCTCG GTGAAGTTA CGCTAGCATT CTGTAAACGG
3481 GCAGCAATCG CCCAGCAGTT AACAAACTGC GCCCACGAGT TCTTCCCTGA CGCCGCTCTC
3541 GCGCAGGCAA GGGAACTCGA TGAATACTAC GCAAAGCACA AGAGACCCGT TGGTCCACTC
3601 CATGGCCTCC CCATCTCTCT CAAAGACCAG CTTCGAGTCA AGGGCTACGA AACATCAATG
3661 GGCTACATCT CATGGCTAAA CAAGTACGAC GAAGGGACT CGGTTCTGAC AACCATGCTC
3721 CGCAAAGCCG GTGCCGTCTT CTACGTCAAG ACCTCTGTCC GCAGACCCT GATGGTCTGC
3781 GAGACAGTCA ACAACATCAT CGGGCGCACC GTCAACCCAC GCAACAAGAA CTGGTCGTGC
3841 GGCGGCAGTT CTGGTGGTGA GGGTGCGATC GTTGGGATTC GTGGTGGCGT CATCGGTGTA
3901 GGAACGGATA TCGGTGGCTC GATTCGAGTG CCGGCCGCGT TCAACTTCCT GTACGGTCTA
3961 AGGCCGAGTC ATGGGCGGCT GCCGTATGCA AAGATGGCGA ACAGCATGGA GGGTCAGGAG
4021 ACGGTGCACA GCGTTGTCGG GCCGATTACG CACTCTGTTG AGGACCTCCG CCTCTTCACC
4081 AAATCCGTCC TCGGTCAGGA GCCATGGAAA TACGACTCCA AGGTCATCCC CATGCCCTGG
4141 CGCCAGTCCG AGTCGGACAT TATTGCCTCC AAGATCAAGA ACGGCGGGCT CAATATCGGC
4201 TACTACAACT TCGACGGCAA TGTCCTTCCA CACCCTCCTA TCCTGCGCGG CGTGGAAACT
4261 ACCGTCGCCG CACTCGCCAA AGCCGGTCAC ACCGTGACCC CGTGGACGCC ATACAAGCAC
4321 GATTTCGGCC ACGATCTCAT CTCCCATATC TACGCGGCTG ACGGCAGCGC CGACGTAATG
4381 CGCGATATCA GTGCATCCGG CGAGCCGGCG ATTCCAAATA TCAAAGACCT ACTGAACCCG
4441 AACATCAAAG CTGTTAACAT GAACGAGCTC TGGGACACGC ATCTCCAGAA GTGGAATTAC
4501 CAGATGGAGT ACCTTGAGAA ATGGCGGGAG GCTGAAGAAA AGGCCGGGAA GGAACTGGAC
4561 GCCATCATCG CGCCGATTAC GCCTACCGCT GCGGTACGGC ATGACCAGTT CCGGTACTAT
4621 GGGTATGCCT CTGTGATCAA CCTGCTGGAT TTCACGAGCG TGGTTGTTCC GGTTACCTTT
4681 GCGGATAAGA ACATCGATAA GAAGAATGAG AGTTTCAAGG CGGTTAGTGA GCTTGATGCC
4741 CTCGTGCAGG AAGAGTATGA TCCGGAGGCG TACCATGGGG CACCGGTTGC AGTGCAGGTT
4801 ATCGGACGGA GACTCAGTGA AGAGAGGACG TTGGCGATTG CAGAGGAAGT GGGGAAGTTG
4861 CTGGGAAATG TGGTGACTCC ATAGCCCGGG GGGGCTCGA TCCCCTCGCG AGTTGGTTCA
4921 GCTGCTGCCT GAGGCTGGAC GACCTCGCGG AGTTCTACCG GCAGTGCAAA TCCGTCGGCA
4981 TCCAGGAAAC CAGCAGCGGC TATCCGCGCA TCCATGCCCC CGAACTGCAG GAGTGGGGAG
5041 GCACGATGGC CGCTTTGGTC GATCTAGATT ACGTGGAAGA AAGGTAGTAA AAGTAGTAGT
5101 ATAAGTAGTA AAAAGAGGTA AAAAGAGAAA ACCGGCTACA TACTAGAGAA GCACGTACAC
5161 AAAAACTCAT AGGCACTTCA TCATACGACA GTTTCTTGAT GCATTATAAT AGTGTATTAG
5221 ATATTTTCAG AAATATGCAT AGAACCTCCT CTTGCCTTTA CTTTTTATAC ATAGAACATT
5281 GGCAGATTTA CTTACACTAC TTTGTTTCTA CGCCATTTCT TTTGTTTTCA ACACTTAGAC
5341 AAGTTGTTGA GAACCGGACT ACTAAAAAGC AATGTTCCCA CTGAAAATCA TGTACCTGCA
5401 GGATAATAAC CCCCTAATTC TGCATCGATC CAGTATGTTT TTTTTTCTCT ACTCATTTTT
5461 ACCTGAAGAT AGAGCTTCTA AAACAAAAAA AATCAGTGAT TACATGCATA TTGTGTGTTC
5521 TAGTAACCAA AGGAAAGGAA CAGATAGATA AAATTCCGAG ACTGTCAAAT TAGGTTTTTT
5581 TCTTTTTTTT TGGCGGGAGT CAGTGGGCCG AAATATGTTC TTGGCCTAGA ACTTAATCTG
5641 GTTTGATCAT GCCAATACTT GCCTGAGTGC CCGACTTTTT GCCCACCCTC TTGCCTTCTG
5701 TCATCCTTCA AAACCCACCT GTTTTCCAGC CGTATCTTCG CTCGCATCTA CACATACTGT
5761 GCCATATCTT GTGTGTAGCC GGACGTGACT ATGACCAAAA ACAAACAAGG AGAACTGTTC
5821 GCCGATTTGT AACACTCCTG CATCCATCCA AGTGGGTATG CGCTATGCAA TGTTAAGCTA
5881 GGTCAGGTCA GACCAGGTCC AAGGACAGCA ACTTGACTGT ATGCAACCTT TACCATCTTT
5941 GCACAGAACA TACTTGTAGC TAGCTAGTTA CACTTATGGA CCGAAAAGGC ACCCCACCAT
6001 GTCTGTCCGG CTTTAGAGTA CGGCCGCAGA CCGCTGATTT GCCTTGCCAA GCAGTAGTCA
6061 CAATGCATCG CATGAGCACA CGGGCACGGG CACGGGCACA GGAACCATTG GCAAAAATAC
```

Figure 7-3

```
6121 CAGATACACT ATACCGACGT ATATCAAGCC CAAGTTTAAA ATTCCTAAAT TTCCGCGGCT
6181 ACTTTTCAAT TCCCTATAGT GAGTCGTATT AAATTCGTAA TCATGTCATA GCTGTTTCCT
6241 GTGTGAAATT GTTATCCGCT CACAATTCCA CACAACATAC GAGCCGGAAG CATAAAGTGT
6301 AAAGCCTGGG GTGCCTAATG AGTGAGCTAA CTCACATTAA TTGCGTTGCG CTCACTGCCC
6361 GCTTTCCAGT CGGGAAACCT GTCGTGCCAG CTGCATTAAT GAATCGGCCA ACGCGCGGGG
6421 AGAGGCGGTT TGCGTATTGG GCGCTCTTCC GCTTCCTCGC TCACTGACTC GCTGCGCTCG
6481 GTCGTTCGGC TGCGGCGAGC GGTATCAGCT CACTCAAAGG CGGTAATACG GTTATCCACA
6541 GAATCAGGGG ATAACGCAGG AAAGAACATG TGAGCAAAAG GCCAGCAAAA GGCCAGGAAC
6601 CGTAAAAAGG CCGCGTTGCT GGCGTTTTTC CATAGGCTCC GCCCCCCTGA CGAGCATCAC
6661 AAAAATCGAC GCTCAAGTCA GAGGTGGCGA AACCCGACAG GACTATAAAG ATACCAGGCG
6721 TTTCCCCCTG GAAGCTCCCT CGTGCGCTCT CCTGTTCCGA CCCTGCCGCT TACCGGATAC
6781 CTGTCCGCCT TTCTCCCTTC GGGAAGCGTG GCGCTTTCTC ATAGCTCACG CTGTAGGTAT
6841 CTCAGTTCGG TGTAGGTCGT TCGCTCCAAG CTGGGCTGTG TGCACGAACC CCCCGTTCAG
6901 CCCGACCGCT GCGCCTTATC CGGTAACTAT CGTCTTGAGT CCAACCCGGT AAGACACGAC
6961 TTATCGCCAC TGGCAGCAGC CACTGGTAAC AGGATTAGCA GAGCGAGGTA TGTAGGCGGT
7021 GCTACAGAGT TCTTGAAGTG GTGGCCTAAC TACGGCTACA CTAGAAGAAC AGTATTTGGT
7081 ATCTGCGCTC TGCTGAAGCC AGTTACCTTC GGAAAAAGAG TTGGTAGCTC TTGATCCGGC
7141 AAACAAACCA CCGCTGGTAG CGGTGGTTTT TTTGTTTGCA AGCAGCAGAT TACGCGCAGA
7201 AAAAAAGGAT CTCAAGAAGA TCCTTTGATC TTTTCTACGG GGTCTGACGC TCAGTGGAAC
7261 GAAAACTCAC GTTAAGGGAT TTTGGTCATG AGATTATCAA AAAGGATCTT CACCTAGATC
7321 CTTTTAAATT AAAAATGAAG TTTTAAATCA ATCTAAAGTA TATATGAGTA AACTTGGTCT
7381 GACAGTTACC AATGCTTAAT CAGTGAGGCA CCTATCTCAG CGATCTGTCT ATTTCGTTCA
7441 TCCATAGTTG CCTGACTCCC CGTCGTGTAG ATAACTACGA TACGGGAGGG CTTACCATCT
7501 GGCCCCAGTG CTGCAATGAT ACCGCGAGAC CCACGCTCAC CGGCTCCAGA TTTATCAGCA
7561 ATAAACCAGC CAGCCGGAAG GGCCGAGCGC AGAAGTGGTC CTGCAACTTT ATCCGCCTCC
7621 ATCCAGTCTA TTAATTGTTG CCGGGAAGCT AGAGTAAGTA GTTCGCCAGT TAATAGTTTG
7681 CGCAACGTTG TTGCCATTGC TACAGGCATC GTGGTGTCAC GCTCGTCGTT TGGTATGGCT
7741 TCATTCAGCT CCGGTTCCCA ACGATCAAGG CGAGTTACAT GATCCCCCAT GTTGTGCAAA
7801 AAAGCGGTTA GCTCCTTCGG TCCTCCGATC GTTGTCAGAA GTAAGTTGGC CGCAGTGTTA
7861 TCACTCATGG TTATGGCAGC ACTGCATAAT TCTCTTACTG TCATGCCATC CGTAAGATGC
7921 TTTTCTGTGA CTGGTGAGTA CTCAACCAAG TCATTCTGAG AATAGTGTAT GCGGCGACCG
7981 AGTTGCTCTT GCCCGGCGTC AATACGGGAT AATACCGCGC CACATAGCAG AACTTTAAAA
8041 GTGCTCATCA TTGGAAAACG TTCTTCGGGG CGAAAACTCT CAAGGATCTT ACCGCTGTTG
8101 AGATCCAGTT CGATGTAACC CACTCGTGCA CCCAACTGAT CTTCAGCATC TTTTACTTTC
8161 ACCAGCGTTT CTGGGTGAGC AAAAACAGGA AGGCAAAATG CCGCAAAAAA GGGAATAAGG
8221 GCGACACGGA AATGTTGAAT ACTCATACTC TTCCTTTTTC AATATTATTG AAGCATTTAT
8281 CAGGGTTATT GTCTCATGAG CGGATACATA TTTGAATGTA TTTAGAAAAA TAAACAAATA
8341 GGGGTTCCGC GCACATTTCC CCGAAAAGTG CCACCTGACG CGCCCTGTAG CGGCGCATTA
8401 AGCGCGGCGG GTGTGGTGGT TACGCGCAGC GTGACCGCTA CACTTGCCAG CGCCCTAGCG
8461 CCCGCTCCTT TCGCTTTCTT CCCTTCCTTT CTCGCCACGT TCGCCGGCTT TCCCCGTCAA
8521 GCTCTAAATC GGGGGCTCCC TTTAGGGTTC CGATTTAGTG CTTTACGGCA CCTCGACCCC
8581 AAAAAACTTG ATTAGGGTGA TGGTTCACGT AGTGGGCCAT CGCCCTGATA GACGGTTTTT
8641 CGCCCTTTGA CGTTGGAGTC CACGTTCTTT AATAGTGGAC TCTTGTTCCA AACTGGAACA
8701 ACACTCAACC CTATCTCGGT CTATTCTTTT GATTTATAAG GGATTTTGCC GATTTCGGCC
8761 TATTGGTTAA AAAATGAGCT GATTTAACAA AAATTTAACG CGAATTTTAA CAAAATATTA
8821 ACGCTTACAA TTTCCATTCG CCATTCAGGC TGCGCAACTG TTGGGAAGGG CGATCGGTGC
8881 GGGCCTCTTC GCTATTACGC CAGCTGGCGA AAGGGGGATG TGCTGCAAGG CGATTAAGTT
8941 GGGTAACGCC AGGGTTTTCC CAGTCACGAC GTTGTAAAAC GACGGCCAGT GCCAAGCTCC
9001 CGCGGGGATC GACTCATAAA ATAGTAACCT TCTAATGCGT ATCTATTGAC TACCAACCAT
9061 TAGTGTGGTT GCAGAAGGCG GAATTCTCCC TTCTTCGAAT TCAGCTTGCT TTTTCATTTT
9121 TTATTTTCCA TTTTTCAGTT TTTGTTTGTG TCGAATTTAG CCAGTTGCTT CTCCAAGATG
```

Figure 7-4

```
 9181 AAAAAAACCC CTGCGCAGTT TCTGTGCTGC AAGATCCTAA TCGACTTTTC CACCCCCCAC
 9241 AAAAGTAAAT GTTCTTTTGT TACATTCGCG TGGGTAGCTA GCTCCCCGAA TCTTCAAAGG
 9301 ACTTAGGGAC TGCACTACAT CAGAGTGTGT TCACCTGGTT TGCTGCCTGG TTTGAAAGAA
 9361 AAGAGCAGGG AACTCGCGGG TTCCCGGCGA ATAATCATGC GATAGTCCTT TGGCCTTCCA
 9421 AGTCGCATGT AGAGTAGACA ACAGACAGGG AGGGCAGGAA GGATCTTTCA CTGAGATCCT
 9481 GTATCTTGTT GGGTAAGTCG GATGAAAGGG GAATCGTATG AGATTGGAGA GGATGCGGAA
 9541 GAGGTAACGC CTTTTGTTAA CTTGTTTAAT TATTATGGGG CAGGCGAGAG GGGGAGGAAT
 9601 GTATGTGTGT GAGGCGGGCG AGACGGAGCC ATCCAGGCCA GGTAGAAATA GAGAAAGCCG
 9661 AATGTTAGAC AATATGGCAG CGTAGTAGAG TAGGTAGGTA GGCAAGTACT GCTAGCAAAG
 9721 AGGAGAAGGG TAAGCTCACT CTTCGCATTC CACACCGTTA GTGTGTCAGT TTGAACAAAA
 9781 AAACAATCAT CATACCAATT GATGGACTGT GGACTGGCTT TTGGAACGGC TTTTCGGACT
 9841 GCGATTATTC GTGAGGAATC AAGGTAGGAA TTTGGTCATA TTTACGGACA ACAGTGGGTG
 9901 ATTCCCATAT GGAGTAGGAA AACGAGATCA TGGTATCCTC AGATATGTTG CGGAATTCTG
 9961 TTCACCGCAA AGTTCAGGGT GCTCTGGTGG GTTTCGGTTG GTCTTTGCTT TGCTTCTCCC
10021 TTGTCTTGCA TGTTAATAAT AGCCTAGCCT GTGAGCCGAA ACTTAGGGTA GGCTTAGTGT
10081 TGGAACGTAC ATATGTATCA CGTTGACTTG GTTAACCAG GCGACCTGGT AGCCAGCCAT
10141 ACCCACACAC GTTTTTTGTA TCTTCAGTAT AGTTGTGAAA AGTGTAGCGG AAATTTGTGG
10201 TCCGAGCAAC AGCGTCTTTT TCTAGTAGTG CGGTCGGTTA CTTGGTTGAC ATTGGTATTT
10261 GGACTTTGTT GCTACACCAT TCACTACTTG AAGTCGAGTG TGAAGGGTAT GATTTCTAGT
10321 GGTGAACACC TTTAGTTACG TAATGTTTTC ATTGCTGTTT TACTTGAGAT TTCGATTGAG
10381 AAAAAGGTAT TTAATAGCTC GAATCAATGT GAGAACAGAG AGAAGATGTT CTTCCCTAAC
10441 TCGAAAGGTA TATGAGGCTT GTGTTTCTTA GGAGAATTAT TATTCTTTTG TTATGTTGCG
10501 CTTGTAGTTG GAAAGGTGA AGAGACAAAA GCTGGAATTG TGAGCGGATA ACAAGCTCAA
10561 CACTTGAAAT TTAGGAAAGA GCAGAATTTG GCAAAAAAAA TAAAAAAAAA ATAAACACAC
10621 ATACTCATCG AG
```

SOLUBILIZATION AND PURIFICATION OF A TARGET PROTEIN FUSED TO A MUTANT MALTOSE-BINDING PROTEIN

CROSS REFERENCE

This application is a §371 application of international application number PCT/US07/09100 filed Apr. 14, 2007, which claims priority from U.S. provisional application number 60/792,133 filed Apr. 14, 2006, herein incorporated by reference.

BACKGROUND

Recombinant proteins have many uses in biotechnology, whenever large amounts of pure protein are needed. Microbial expression systems such as *Escherichia coli* (*E. coli*) and yeast are often the first choice due to their low cost and high yield. When expressing foreign proteins in *E. coli*, it is not uncommon to encounter problems of low levels of expression and/or insolubility of the protein. Even if the protein is expressed well and remains soluble, it must be purified from the myriad of other proteins in the cell extract. To facilitate the expression and purification of a target protein, one method that is in common use is to fuse an affinity tag to the protein. A good affinity tag has properties that facilitate high-level expression when fused to the N-terminus of the target protein, as well as providing a simple one-step affinity purification that allows the target protein to be purified from the expression mileu.

The maltose-binding protein (MBP) of *E. coli* is commonly used as an affinity tag for expression and purification of foreign proteins produced in *E. coli*. The natural role of MBP is to bind maltodextrins at the outer membrane porin and release them to the MalEFK transport apparatus in the inner membrane. Fusion of the C-terminus of MBP to the N-terminus of a target protein permits the expression of the fusion protein in *E. coli* (FIG. 1). MBP and MBP fusions can be purified in a single step by binding to a chromatography matrix containing any of a number of glucose-α1→4-glucose polysaccharides such as amylose, starch or other maltodextrins (U.S. Pat. No. 5,643,758). Many proteins that are soluble in their native host are insoluble when expressed as a recombinant protein. For many of these proteins, fusion to MBP renders them soluble (Kapust & Waugh, *Protein Sci.* 8:1668-74 (1999)).

The utility of MBP as an affinity tag is tempered by the fact that depending on the protein in a MBP-target protein purification, some fusions don't bind to the affinity matrix as well as others. In addition, the presence of non-ionic detergents such as Triton X100 and Tween 20 can interfere with binding, especially for MBP-target protein fusions that have an inherently lower affinity.

Researchers have used the structure of MBP to make directed to mutations in order to alter the binding properties of MBP. The X-ray crystal structure of MBP has been reported by Spurlino et al., *J. Biol. Chem.* 266:5202-5219 (1991). MBP consists of two domains, with a cleft between the domains where the polysaccharide binds. The domain that contains the N-terminus is named the N domain, and the domain that contains the C-terminus is named the C domain. Three loops cross between the two domains to form a hinge. Two groups have used the structure to make directed mutations to the region behind the hinges that increase the affinity of MBP for maltose and maltotriose (Marvin et al., *Nature Structural Biology* 8:795-798 (2001); Telmer & Shilton, *Journal of Biol. Chem.* 278:34555-34567 (2003)). However, this approach has an inherent disadvantage, since the modifications to MBP increase the hydrophobicity of the surface of the protein and thus decrease its solubility. This reduces its utility as an affinity tag by increasing its tendency to render a fusion protein insoluble.

SUMMARY

In an embodiment of the invention, a modified MBP fusion protein is provided that is characterized by an MBP amino acid sequence having a mutation wherein the mutation causes the modified MBP fusion protein to have at least one property selected from (i) an increased affinity for a maltodextrin substrate and (ii) an increased solubility when fused to a target protein having limited solubility. In a further embodiment of the invention, the modified MBP has a mutation located in the hinge region between helices XI and XII or in a region within 10 Å of A313 of the protein. For example, the mutation may be located in the C domain or in a region within 10 Å of S146, at the beginning of β-sheet F of the protein. The modification may be specifically A313V or S146T.

In a further embodiment of the invention, the modified MBP may be fused to a target protein to form a fusion protein and may, for example, have a solubility that is greater than the solubility of an unmodified MBP protein fused to the target protein.

In an embodiment of the invention, the modified MBP may have an amino acid sequence selected from SEQ ID NO:4 or SEQ ID NO:6 or a DNA sequence encoding the protein selected from SEQ ID NO:3 or SEQ ID NO:5. The DNA may be incorporated into a vector such as a pKLAC1 vector for expression in a host cell such as a *Kluyveromyces* or *E. coli*.

In an embodiment of the invention, a method is provided for purifying a protein that includes: expressing in a host cell such as a *Kluyveromyces* or *E. coli*, a fusion protein that includes any of the modified MBPs described above and a target protein. The modified MBP fusion protein is permitted to bind to a matrix such as a polysaccharide exemplified by a maltodextrin. The fusion protein can then be eluted from the matrix in a selected buffer to obtain the purified protein.

In a further embodiment of the invention, a method is provided for solubilizing a target protein that includes expressing an MBP mutant fused to a target protein so that the fusion protein is solubilized to an extent greater than can be observed in the absence of the mutant MBP and to an extent greater than observed using a non-mutated MBP. Examples of mutations include a A313V mutation and/or an S146T mutation.

BRIEF DESCRIPTION OF THE DRAWINGS

FIGS. 2A-1 to 2A-2, 2B-1 to 2B-2, and 2C-1 to 2C-2 provide sequences comparing wild-type MBPs with modified MBPs.

FIGS. 2A-1 to 2A-2: The DNA sequence (SEQ ID NO:1) encoding wild-type MBP (SEQ ID NO:2) from pMAL-c2X.

FIGS. 2B-1 through 2B-2: The DNA sequence (SEQ ID NO:3) encoding the MBP mutant A9 (SEQ ID NO:4). Changes in the modified MBP sequences are indicated in bold.

FIGS. 2C-1 through 2C-2: The DNA sequence (SEQ ID NO:5) encoding the MBP mutant G8-1 (SEQ ID NO:6). Changes in the modified MBP sequences are indicated in bold.

FIGS. 5-1 to 5-5. Sequence of pMB50 (SEQ ID NO:7) used for expressing MBP-CBD fusion protein (see Table 2).

FIGS. 7-1 to 7-4 provide the sequence of pKLMF2-PMΔ-Sal (SEQ ID NO:8).

Figure 1:
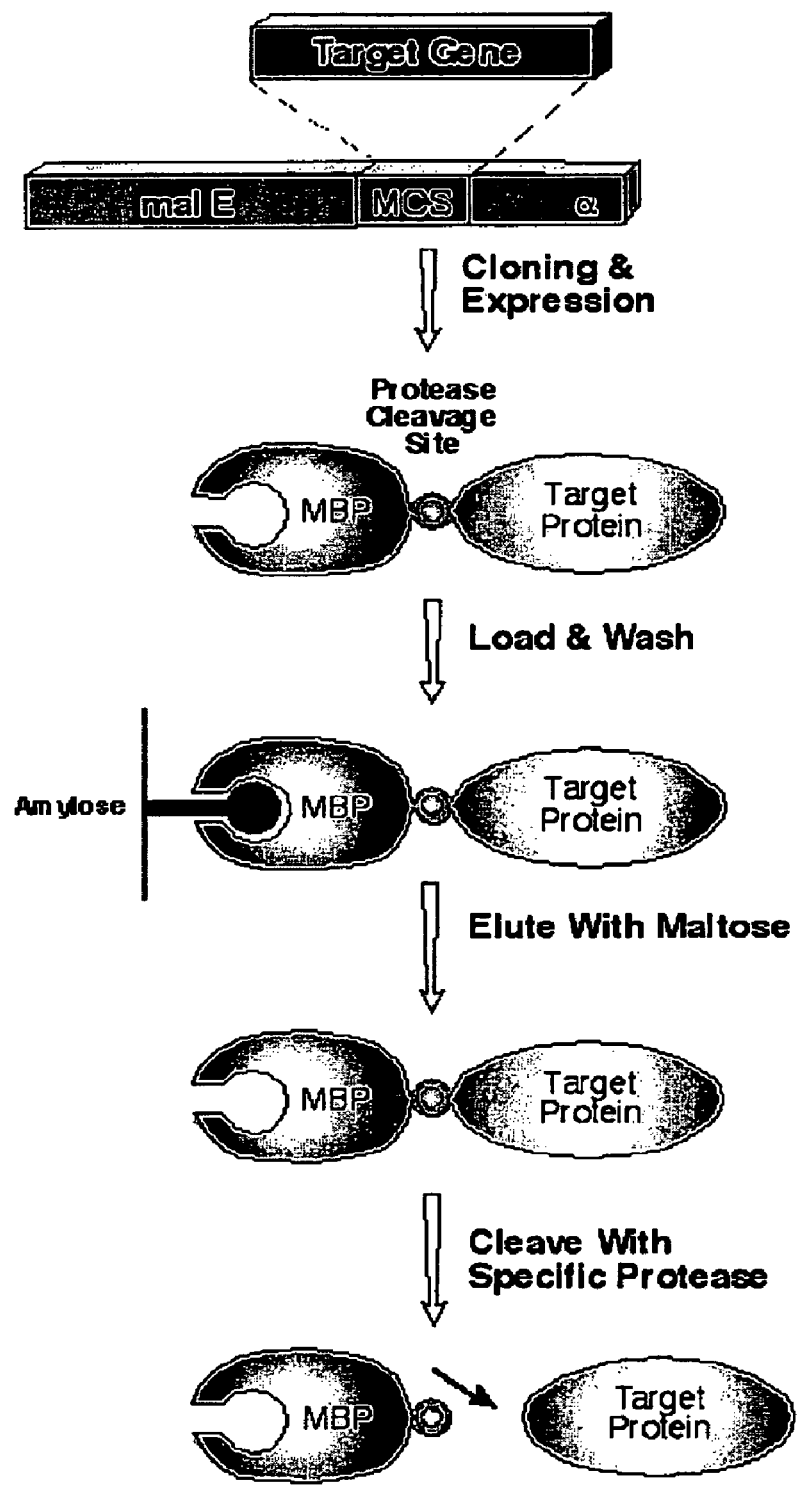
FIG. 1 shows a schematic describing the cloning and purification of a target protein by expressing a DNA encoding an MBP fused to a target protein, allowing the fusion protein to selectively bind to amylose, eluting the target protein in a maltose-containing buffer and then recovering the target protein from the purified fusion protein by protease cleavage.

Lane 1-NEB Broad range markers, Ipswich, Mass.;
Lane 2-crude extract load;
Lane 3-column flow-through;
Lane 4-column wash;
Lanes 5, 6 and 7, elution with column buffer+maltose.

DETAILED DESCRIPTION OF THE EMBODIMENTS

Terms that are used herein are discussed below.

"Wild-type" MBP includes the MBP protein produced by expression from a derivative of one of the pMAL-2 plasmids that has a stop codon in the polylinker, for example pKO1483.

"Enhanced solubility of a protein fused to a mutant MBP" is an increase in the amount of soluble protein when compared to that same protein fused to wild-type MBP. Solubility can be expressed as the ratio of soluble protein to the total amount of that protein present before insoluble material is removed, for example by centrifugation.

"Increased affinity of a mutant MBP" or "mutant MBP fusion protein" includes: an increase in the amount of protein that binds to a solid substrate such as a maltodextrin under a defined set of conditions. The efficacy of the affinity purification can be expressed as the ratio of protein that binds to maltodextrin under the specified conditions and is then eluted with a specified buffer to the total amount of that protein applied to the column.

The present embodiments of the invention provide MBP mutants which when fused to a target protein enhance the solubility of the fusion protein during expression in vivo and can also improve the affinity of the fusion protein during purification. The present embodiments include mutant MBPs that show increased binding to a polysaccharide media, such as one that includes a maltodextrin, when applied to the media under conditions where wild-type MBP shows partial binding. The modified MBPs are then eluted from the media using a solution of, for example, a soluble maltodextrin, yielding at least 1.5 to 10-fold more protein when compared to wild-type MBP.

In order to discover these improved mutants of MBP, technical hurdles had to be overcome which include developing techniques which enable a large number of samples to be handled. This required improved methods for breaking up host cells to release solubilized fusion protein where sonication is not practical for large scale purification and lysis buffers could interfere with affinity binding of MBP. It was discovered that by titrating the detergent and the lysozyme, it was possible to identify the appropriate concentration and ratio of these lysis reagents to effectively break up host cells without negatively impacting binding affinity.

In order to screen for mutants with desired binding affinity properties, 96 well microplates were used where each well contained a micro matrix for binding fusion protein and a filter apparatus removed contaminating materials in the filtrate. This made possible rapid screening of large numbers of samples.

The screening methods for obtaining and testing modified mutant MBP proteins as improved tags for purifying proteins are described in the examples. Such modified MBPs that have a higher affinity for a matrix solve the problem associated with wild-type MBP of MBP fusions proteins that bind poorly to a matrix or where binding is disrupted by the presence of non-ionic detergent.

In the examples, two mutations (S146T and A313V) are described with the desired properties of improved solubility and improved binding affinity to a polysaccharide matrix that were isolated using the screening procedure. The S146T mutation is in the C domain of MBP at the beginning of β-sheet F. When a target protein that is insoluble is fused to MBP containing this mutation, the solubility of the fusion protein is enhanced. The A313V mutation described herein is located in the third hinge region that crosses between the two domains, specifically, in the loop between helices XI and XII. This mutation enhances both the solubility and the affinity of fusion proteins. When expressing foreign proteins in *E. coli*, the protein may be partially or completely expressed in the form of insoluble aggregates. In particular examples, solubility may be increased by 1.1 or greater upwards with an upper limit of total solubility.

All references cited herein, as well as U.S. provisional application No. 60/792,133 filed Apr. 14, 2006, are incorporated by reference.

EXAMPLES

Materials

Restriction enzymes, β-agarase, DNA polymerases, T4 ligase, Antarctic phosphatase, Litmus 38, the pMAL Protein Fusion and Purification System including pMAL-c2X and pMAL-c2G, amylose resin (#E8021), anti-MBP monoclonal antibody linked to horse radish peroxidase (#E8038), the USER Friendly Cloning kit, the *K. lactis* Protein Expression Kit including the vector pKLAC1, host strains TB1, ER1992, ER2502, ER2984, NEB 5-alpha, and NEB Turbo, and synthetic oligonucleotides were obtained from New England Biolabs, Inc. (NEB), Ipswich, Mass. Unifilter 800 microtiter microplates with filter bottoms were purchased from Whatman, Brentford, England. The Minelute DNA Extraction and Qiaprep Spin kits were purchased from Qiagen, Valencia, Calif. Mega 10 was purchased from Dojindo, Gaithersburg, Md. Hen egg white lysozyme, Coomassie brilliant blue R and acid washed glass beads (425-600 micron) were purchased from Sigma-Aldrich, St. Louis, Mo. Sea Plaque GTG low melting temperature agarose was purchased from Cambrex, E. Rutherford, N.J. Disposable polypropylene columns (#732-6008) were purchased from BioRad, Hercules, Calif. 10-20% gradient gels were purchased from either Daiichi, Tokyo, Japan or InVitrogen/Novex, Carlsbad, Calif. The Complete™ protease inhibitor cocktail was purchased from Roche, Basel, Switzerland. SimplyBlue Safestain was purchased from Invitrogen, Carlsbad, Calif. The human dihydrofolate reductase (DHFR) cDNA clone pOTB7-DHFR was purchased from Invitrogen (MGC:857). The GAPDH gene was obtained from pJF931 (Fox et al. *FEBS Lett.* 537:53-57 (2003).

Techniques

The *Serratia marscesens* nuclease was obtained as described in PCT/US05/28739. Minipreps of plasmid DNA were prepared using the Qiaprep Spin kit. Random PCR mutagenesis was carried out as described in Fromant et al. *Analytical Biochemistry* 224, 347-353 (1995). PCR was carried out using Vent® DNA polymerase except as noted. DNA fragments were gel-purified by electrophoresis on 1% Sea Plaque GTG low melting temperature agarose, cutting out the band, and either purifying the DNA using the Minelute DNA Extraction kit, or melting it at 75° C. for 5 minutes, cooling to 37° C., and digesting with β-agarOse for 1-2 h. DNA sequencing was performed on Applied Biosystems's (ABI's) automated DNA Sequencer model 3100 ABI, using Big Dye labeled dye-terminator chemistry (ABI, Foster City, Calif.). SDS-PAGE was carried out according to the instructions of the acrylamide gel provider, and proteins were visualized by staining with Coomassie brilliant blue R except where noted otherwise.

MBP was expressed from either pMal-c2X or pMal-c2G or a derivative of pMal-c2G. The numbering of bases to identify mutations in malE refers to the base number in the pMAL-c2X sequence ((FIGS. 2A-1, 2A-2, 2B-1, 2B-2, 2C-1 and 2C-2 (SEQ ID NOS:1-6)). The pMAL-c2G derivative pSN1578 was created by cleaving the plasmid with BsmI and BsiWI, treating the product with DNA polymerase Klenow fragment plus all four dNTPs, followed by ligation to create a deletion within the malE gene.

Site-directed mutagenesis was carried out using a four primer PCR mutagenesis as described in Guan et al. *Nucleic Acid Research*, 33:6225-6234 (2005). MBP and MBP fusion proteins were purified as described in the instructions for the pMAL Protein Fusion and Purification System, except in some cases cells were lysed with a lysozyme/detergent solution instead of sonication.

Large-scale purifications were carried out with crude cell extract prepared from 500 to 1000 mL of culture, and loaded on a 2.5 cm diameter column containing 15 ml of amylose resin (NEB #E8021, Ipswich, Mass.). Small-scale purifications were carried out with crude extract prepared from 67 ml of culture, and loaded on a disposable polypropylene column containing 1 ml of amylose resin. SDS-polyacrylamide gel electrophoresis was carried out using 10-20% gradient gels. For quantitation of gel bands, gels were dried between cellophane sheets and scanned using a Microtek III scanner Microtek, Carson, Calif., and densitometry carried out using Image J (NIH).

Example I

Isolation of Mutants in MBP with Improved Properties

Screening for Improved Yield after Purification:

Random mutagenesis of the malE gene from pMAL-c2x was achieved by error-prone PCR using the primers:

```
                                          (SEQ ID NO: 9)
oligo 1: 5' GGAGACAUGAATTCAATGAAAATCGAAGAA,
and (SEQ ID NO: 10)
oligo 2: 5' GGGAAAGUAAGCTTAATCCTTCCCTCGATC
```

PCR fragments were cloned into linearized pNEB208A using the USER Friendly Cloning Kit, following the manufacturer's instructions. Transformants were grown overnight in 1 mL LB+1 mM IPTG and 100 ug/ml ampicillin, then lysed by adding 0.3 mg/mL lysozyme and 20 units of the *S. marscens* nuclease, incubating for 10 min, then adding 0.1 ml of 2% Tween 20.

The crude extracts were applied to a 50 uL amylose resin column (NEB #E8021, Ipswich, Mass.) in a Unifilter 800 microplate, and each well was washed with 0.7 ml of 20 mM Tris-Cl, 0.2 M NaCl, 1 mM EDTA, pH 7.4 (column buffer), then with 0.7 mL of 10 mM sodium phosphate, 0.2 M NaCl, 1 mM EDTA, pH 7.2. The protein bound to the amylose resin was then eluted with 0.2 mL of 10 mM maltose, 10 mM sodium phosphate, 0.2 M NaCl, 1 mM EDTA, pH 7.2. The eluate was transferred to an Immulon 2HB microtiter plate (ThermoFisher Scientific, Waltham, Mass.) and incubated overnight at 4° C. The microtiter wells were then emptied, washed twice with 20 mM Tris-Cl, 150 mM NaCl, pH 7.5 (TBST), then blocked with 0.36 ml TBST+3% bovine serum albumin for 1 h at 37° C.

The wells were washed twice with TBST, then 0.1 ml of a 1:2000 dilution of anti-MBP monoclonal antibody linked to horse radish peroxidase in TBST+3% bovine serum albumin was added to each well and the plate incubated at 37° C. for 1 h. The wells were emptied, then washed twice with TBST. The wells were developed with 0.01% o-phenylenediamine, 0.003% hydrogen peroxide in water. The detection reaction was stopped by adding 0.025 mL 4 M $H_2SO_4$, and wells were assayed spectrophotometrically at 490 nm. Cells were recovered from lysates corresponding to samples that showed higher binding and elution as compared to wild-type MBP. These candidates were grown and retested to confirm the higher binding and elution.

Characterization and Separation of Mutations Obtained after Random Mutagenesis

Two isolates from a library in USER having increased binding and elution profiles were sequenced (FIG. 2). One isolate, G8-1, was found to have a single mis-sense mutation, G1964C, along with a silent mutation. The G1964C mutation corresponds to the amino acid change S146T in MBP. The other isolate, A9 was found to have three mis-sense mutations, A1583G, A2419G and C2465T, along with a silent mutation. The A1583G, A2419G and C2465T mutations correspond to the amino acid changes N19S, K298E and A313V, respectively.

Subcloning into pMal-C2X or pSN1578

Each isolate was amplified by PCR with the following primers:

```
oligo 3:
                                         (SEQ ID NO: 11)
5' GACTCATATGAAAATCGAAGAAGGTAAACTGGTAATCTGGATTAAC
GGC
and oligo 4:
                                         (SEQ ID NO: 12)
5' ATATAAGCTTTCACCTTCCCTCGATCCCGAGGT
```

Figure 3:
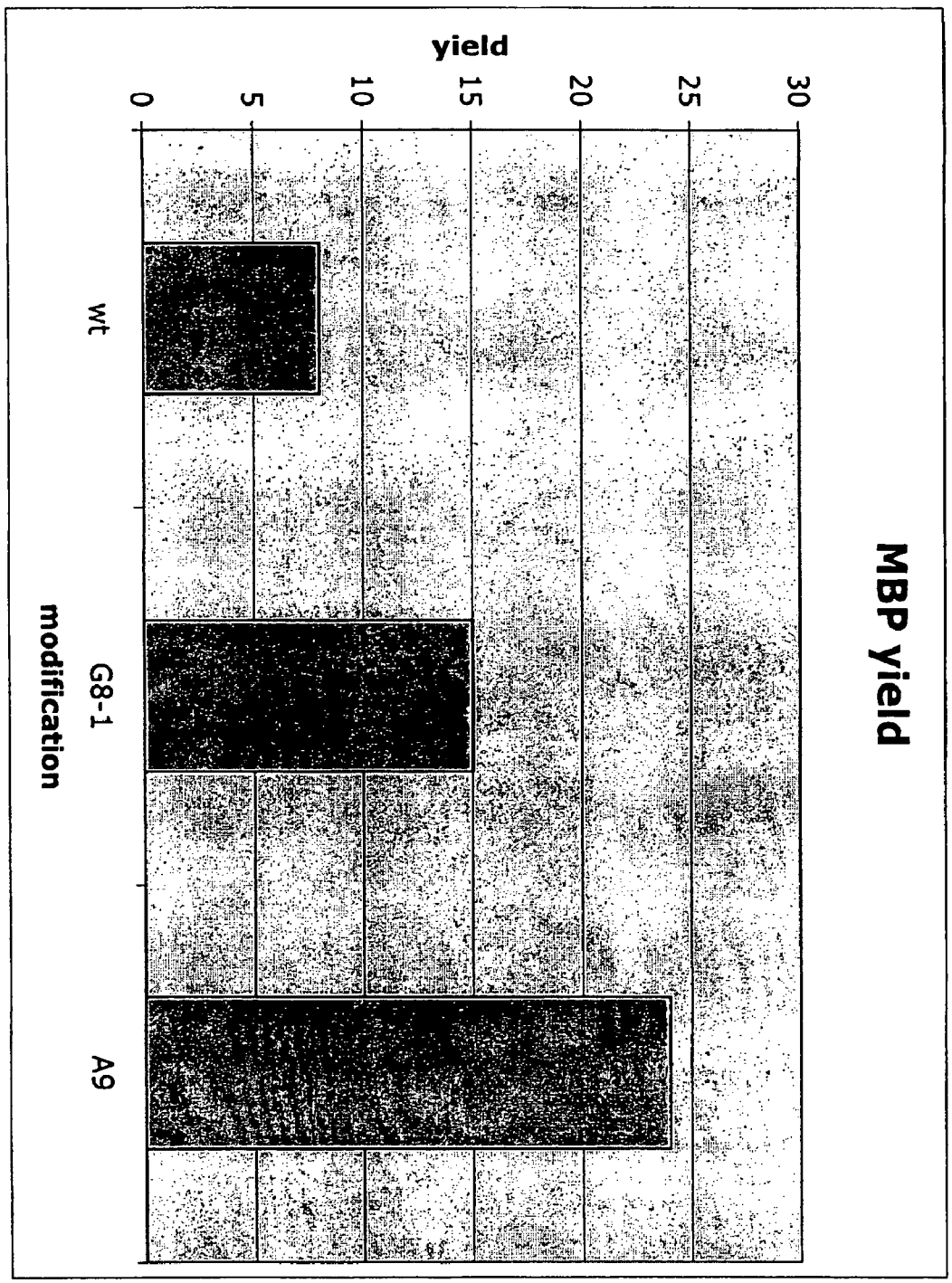
FIG. 3 shows a histogram comparing yields of protein using wild-type MBP (pKO1483), or modified MBPs (A9 or G8-1). The yields of MBPs are provided in mg/500 mls of culture.

The amplified DNA was ethanol precipitated, cut with NdeI and HindIII in NEBuffer 4 (NEB, Ipswich, Mass.), and gel purified. pSN1578 was cleaved with NdeI and HindIII and the vector backbone was gel purified. The G8-1 and A9 fragments were mixed with the pSN1578 fragment and ligated, and the ligation was used to transform TB1. A plasmid preparation from each transformant was sequenced and named pIH1596 for G8-1 and pIH1593 for A9. The 3' primer in this experiment has a stop codon in the correct reading frame to prevent malE translation from proceeding into the lacZα fragment of pMAL. Thus, these subclones produce a modified MBP that ends after the amino acid sequence . . . IEGR encoded by the polylinker. A control plasmid containing a wild-type malE gene followed by a stop codon was constructed by cleaving pMAL-c2X in the polylinker between malE and LacZa with XbaI. The XbaI overhang was filled in using DNA polymerase I, large fragment (Klenow) and all four dNTP's, then the plasmid was recircularized by treatment with T4 ligase. This introduces a stop codon in the same reading frame as malE, and this derivative produces an MBP comparable to that produced by G8-1 and A9, except for an 8 residue extension encoded by the polylinker. This control plasmid was named pKO1483. E. coli TB1 containing pKO1483, pIH1596 and pIH1593 were grown in a 500 mL culture of LB+0.1% glucose and 100 ug/ml ampicillin to $2 \times 10^8$ cells/ml, induced with 0.3 mM IPTG, grown for 2 h at 37° C., then harvested. The cells were resuspended in 25 ml column buffer (0.2 mL of 10 mM maltose, 10 mM sodium phosphate, 0.2 M NaCl, 1 mM EDTA, pH 7.2)+10 mM β-mercaptoethanol, then lysed by sonication. The extract was clarified by centrifuging at 9000×g for 30 min, then diluted 1:4 with column buffer and loaded onto a 15 ml column of amylose resin. The column was washed with about 125 mL column buffer, and eluted with column buffer+10 mM maltose. The yields of MBP were compared among the three strains (FIG. 3). The results confirm that the modified MBPs showed an increased binding to amylose and elution in appropriate buffers.

In order to ascertain which of the three mutation(s) were necessary for increased binding of the A9 variant, the three mutations were subcloned separately into pSN1578, a pMAL-c2G derivative with a deletion internal to the malE gene (which allows easy identification of clones which receive an insert). The A1583G and A2419G mutations either had no effect or reduced the yield of MBP in the affinity purification, and were discarded. The C2465T mutation was recreated in isolation by 4 primer site-directed PCR mutagenesis using pMAL-c2X as the first template, with the primers oligo 5: 5'CTTCAAGGGTCAACCATCCAAACC (SEQ ID NO:13) and oligo 6: 5'AATACGCGGATCTTTCAC-CAACTCTTC (SEQ ID NO:14) to create the N-terminal PCR fragment, and with primers oligo 7: 5' GAAGAGTTG-GTGAAAGATCCGCGTATT (SEQ ID NO:15) and oligo 8: 5'CTGAGAATTCTGAAATCCTTCCCTCGAT (SEQ ID NO:16) to create the C-terminal PCR fragment. The assembly step was carried out with the gel-purified N- and C-terminal fragments as the template and the primers oligo 5 and oligo 8. The final PCR fragment was cut with BlpI and AvaI, gel purified, and ligated to pMAL-c2X that had been cut with BlpI and AvaI and gel purified. The ligation was used to transform TB1, and plasmid was purified from the transformants and sequenced to confirm the C2465T mutation. An isolate was chosen for further study and named pIH1606.

In the construction of pIH1606, the stop codon at the end of MBP was not conserved; this construct expresses MBP fused to the LacZaa fragment. In order to compare the effect of the C2465T mutation to its parent, A9, a stop codon was introduced after the malE gene in pIH1606. The plasmid was cleaved with XbaI, filled in with Klenow plus dNTP's, and religated as described above for pKO1483. The C2465T derivative with a stop codon was called pPR1610. Large scale MBP purifications of TB1 bearing this plasmid, in parallel with pKO1483 and A9, showed that all of the increase in yield of MBP found in A9 could be accounted for by the C2465T mutation. This mutation changes alanine 313 of MBP to a valine (A313V).

In order to be able to compare MBP (S146T) to wild-type MBP and MBP (A313V) in derivatives that have exactly parallel construction, a version of MBP (S146T) was constructed that has the same stop codon as pKO1483 was constructed. An NdeI, BlpI fragment from pIH1596 was purified and subcloned into pKO1493 cut with NdeI and BlpI, creating pIH1619.

Example II

Increased Yield of MBP Fusion Proteins

A: MBP-Klenow

In order to test if the modified MBPs can increase the yield of a fusion protein after purification, the gene encoding the Klenow fragment of E. coli DNA polymerase I was cloned into pMAL-c2X, pIH1619 (S146T) and pPR1610 (A313V). The MBP-Klenow fusion was chosen because it has an inherently low affinity for the amylose column, and during the affinity purification some of the MBP-Klenow protein flows though the amylose column without binding. The Klenow portion of DNA polymerase I was PCR'd from the plasmid pPolA, which contains the BglII-HindIII fragment of the polA gene (Genbank ecopolA: 206-4127) cloned into pBR322 between the BglII and HindIII sites. PCR was carried out using the primers

```
                                        ((SEQ ID NO: 17)
   oligo 9: 5' CCAGAAGTGACGGCAACGGTGATT
   and (SEQ ID NO:18)
   oligo 10: 5' AAGTGCGGCGACGATAGTCATGCCCCGCGC.
```

The PCR fragment was cleaved with HindIII and ligated to pMAL-c2, which had been cleaved with XmnI and HindIII. The resulting construct was named pIH1040. In order to reduce the chance of PCR errors in the insert, the region from XhoI to HindIII was replaced with the corresponding fragment from pPolA. This construct was checked by sequencing and named pIH1062. The gene encoding the Klenow fragment was cloned into pPR1610 and pIH1619 by PCR using pPolA as a template and the primers

```
oligo 11: 5' GTGATTTCTTATGACAACTACGTCACCATCCTTGATG       (SEQ ID NO: 19)
and oligo 12: 5' TTAAGGATCCTTAGTGCGCCTGATCCCAGT             (SEQ ID NO: 20)
```

The PCR fragment was cleaved with BamHI, and the vectors were cleaved with XmnI and BamHI, purified, mixed with the PCR fragment, and ligated. The ligation was used to transform NEB Turbo (Ipswich, Mass.), and transformants were checked for the correct structure by restriction analysis and by expression of the MBP-Klenow fusion and analyzing by SDS-PAGE. The pIH1610-Klenow construct was named pIH1643, and the pIH1619-Klenow construct was named pIH1644.

Figure 4:
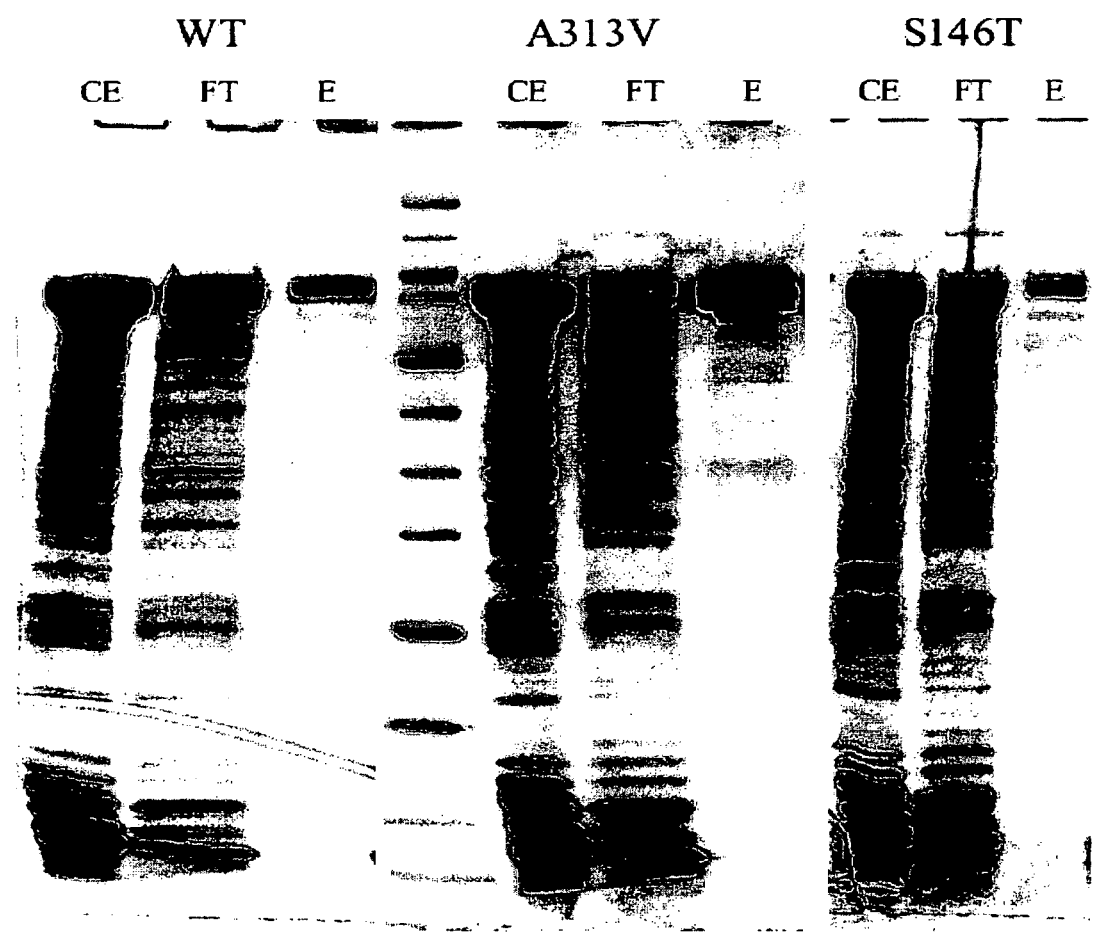
FIG. 4 shows on an SDS-PAGE gel the purified product of MBP-Klenow from pMAL containing wild-type MBP, MBP A313V and S146T modifications. Plasmids: WT=pIH1062, A313V=pIH1643, S136T=pIH1644. Lanes: CE=crude extract, FT=flow though, and E=eluate. Equal portions of the indicated fraction were loaded in each lane. A significantly higher yield of MBP fusion protein was obtained from A313V mutant MBP than from wild-type MBP (also see Table 1).

Affinity purification of MBP-Klenow was performed using cells containing pIH1062, pIH1643 and pIH1644. Crude extract, column flow-through and eluate fractions from each strain were analyzed by SDS-PAGE (FIG. 4). The eluted protein was quantitated by measuring $A_{280}$ and quantitated using the predicted extinction coefficient of the MBP-Klenow protein (Table 1). Cells bearing pIH1643, carrying the MBP-A313V modification, yielded more than twice as much fusion protein as those containing the wild-type MBP or the S146T modified MBP fusion plasmids.

B. MBP-Chitin Binding Domain:

In order to test if the mutant MBP's ability to increase the yield of fusion protein from the affinity purification was a general property, another fusion protein that has an inherently low affinity for amylose was tested. The MBP fused to the Bacillus circulans chitin binding domain (MBP-CBD) is encoded by the plasmid pMB50 (FIG. 5). A good fraction of this MBP-CBD fusion protein tends to flow through an amylose column during the affinity purification, similar to MBP-Klenow. The portion of pPR1610 encoding MBP(A313V) was cleaved from the plasmid using HpaI and SacI, and the fragment was purified. pMB50 was cleaved with the same enzymes, the backbone was also purified, and the two fragments were ligated and transformed into ER2523. The resulting plasmid was named pIH1660.

Affinity purification of MBP-CBD was performed using cells containing pMB50 and pIH1660 harvested from 500 mL cultures. The eluted protein was quantitated by measuring $A_{280}$ and using the predicted extinction coefficient of the MBP-CBD protein (Table 2). Cells bearing pIH1660, carrying the MBP-A313V modification, yielded almost twice as much fusion protein as those containing the wild-type MBP fusion plasmid.

Example III

Solubility Enhancement of MBP Fusion Proteins

Construction of MBP Fusions

In order to test whether the modified MBP's retained the ability to enhance the solubility of the protein fused to MBP, two proteins that tend to be insoluble in E. coli, dihydrofolate reductase (DHFR) and glyceraldehyde-3-phosphate dehydrogenase (GAPDH), were cloned into pIH1619 (S146T) and pIH1610 (A313V). As controls, the same two proteins were cloned into pMAL-c2X and a pMAL-c2G derivative containing the mutations in the Telmer et al. modified MBP named "MBP-DM." The vector encoding MBP-DM was constructed as follows: First, a pMAL-c2G derivative with a translationally silent NsiI site at nucleotide 2030 was constructed by four primer site-directed PCR. The template for both the N- and C-terminal fragments was pMAL-c2X. The primers oligo 13: 5'CCATAGCATATGAAAATCGAAGAAG (SEQ ID NO:21) and oligo 14: 5'CTTGAATGCATAACCCCCGT-CAGCAGC (SEQ ID NO:22) were used to create the N-terminal fragment, and the primers oligo 15: 5' GGTTATGCAT-TCAAGTATGAAAACGGCAAG (SEQ ID NO:23) and oligo 8 were used to create the C-terminal fragment. The PCR fragments were gel purified, then used as a template in the assembly step with the primers oligo 13 and oligo 8. The final PCR fragment was ethanol precipitated, cleaved with NdeI and EcoRI, and gel purified. pMAL-c2X was cleaved with NdeI and EcoRI and gel purified, and the two fragments were mixed and ligated. The ligation was used to transform ER2502, overnight cultures were grown, and miniprep DNA prepared. Several transformants that had acquired the NsiI site and were of the correct size were obtained, but unexpectedly, all of them lacked an EcoRI site. A representative of this set, named pPR1629, was cleaved with NdeI and AvaI, and the malE fragment was gel purified. pSN1578 was cleaved with the same two enzymes and the plasmid backbone was gel purified. These two DNA fragments were ligated, the ligation was used to transform ER2502, and plasmid DNA from one transformant was sequenced, and named pPR1633. Second, the gene for the modified MBP called DM by Telmer and Shilton was constructed by four primer PCR site-directed mutagenesis as follows: The template for both the N- and C-terminal fragments was pMAL-c2X. The primers used for the N-terminal fragment were oligo 16: 5' TATGCATTCAAATACGGTGACATTAAA-GACGTGGGCGTGGAT (SEQ ID NO:24) and oligo 17: 5' GCGGCGTTTTCCGCAGTGGCGGCAATACGTGGAT-CTTTC (SEQ ID NO:25). The C-terminal fragment was produced with the primers oligo 18: 5' GCGGAAAACGCCGC-GAAAGGTGAAATCATGCCGAACATC (SEQ ID NO:26) and oligo 8. The assembly PCR was performed using the purified N- and C-terminal fragments with oligo 16 and oligo 8 as the primers. The PCR fragment was ethanol precipitated and ligated to Litmus 38 that had been linearized with EcoRV and treated with Antarctic phosphatase. The ligation was used to transform NEB 5-alpha (Ipswich, Mass.), and plasmid DNA from one transformant was sequenced to confirm the construction and named pPR1638. Plasmid DNAs pPR1633 and pPR1638 were cleaved with NsiI and AvaI, the plasmid backbone from pPR1633 and the 'malE fragment from pPR1638 were gel purified, ligated, and the ligation was used to transform NEB Turbo. Plasmid DNA from one transformant was selected for sequencing and named pPR1639.

The DHFR gene was PCR'd using pOTB7-DHFR as a template and using the primers oligo 19: 5' GGATGGTTG-GTTCGCTAAACTGCATCGTC (SEQ ID NO:27) and oligo 20: 5' TATTAATCATTCTTCTCATATACTTCAAA (SEQ ID NO:28), then treating the PCR fragment with T4 polymerase and dT for 15 m at room temperature. This treatment produces a short 3' overhang on each end of the fragment, a GG on the upstream end of the DHFR gene, and an A on the downstream end. The vectors pMAL-c2X and pPR1610 were prepared by cleaving with XmnI, then treating with T4 polymerase and dA, which likewise produces a 3'CC overhang at the end of the malE region and a T on the LacZa end. The vector DNAs were ligated to the DHFR fragment and the ligation was used to transform ER1992. For each vector, a transformant was confirmed by restriction analysis and expression of a fusion protein of the expected size analyzed by SDS-PAGE. The pMAL-c2X-DHFR isolate was named pIH1616, and the pPR1610-DHFR isolate was named pIH1617. The DHFR insert was then subcloned into pIH1596 as follows: pIH1616 was cleaved with NdeI and BlpI, the digest run on a gel, and the backbone (including the DHFR gene) was cut out and gel purified. pIH1596 was cut with NdeI and BlpI, and the malE' was gel purified. The vector backbone was ligated to the malE' fragment, and the ligations used to transform ER1992. An isolate was confirmed by restriction analysis and expression of a fusion protein of the expected size analyzed by SDS-PAGE, and named pIH1618. The DHFR insert was subloned into pPR1639 by cleaving both pPR1639 and pIH1616 with AvaI and SalI, gel purifying the vector backbone from pPR1639 and the DHFR fragment from pIH1616, and ligating the two fragments. The ligation was used to transform NEB Turbo, and a transformant was confirmed by sequencing and named pIH1646.

The GAPDH gene was subjected to PCR using pJF931 as a template and using the primers oligo 21: 5' GGATGGTGAAGGTCGGTGTGAACGG (SEQ ID NO:29) and oligo 22: 5' TATTACTCCTTGGAG-GCCATGTAGGCCA (SEQ ID NO:30), then treating the PCR fragment with T4 polymerase and dT.

The vectors pMAL-c2X, pPR1610 and pIH1619 were prepared by cleaving with XmnI, then treating with T4 polymerase and dA as described above. The vector DNAs were ligated to the GAPDH fragment and the ligation was used to transform ER1992. For each vector, a transformant was confirmed by restriction analysis and expression of a fusion protein of the expected size analyzed by SDS-PAGE. The pMAL-c2X-GAPDH isolate was named pIH1625, the pPR1610-GAPDH isolate was named pIH1626, and the pIH1619-GAPDH isolate was named pIH1627. The GAPDH insert was then subcloned into pPR1639 by cleaving both pPR1639 and pIH1625 with AvaI and SalI, gel purifying the vector backbone from pPR1639 and the GAPDH fragment from pIH1625, and ligating the two fragments. The ligation was used to transform NEB Turbo, and a transformant was confirmed by restriction analysis and expression of a fusion protein of the expected size analyzed by SDS-PAGE, and named pIH1645.

Solubility Profile

A 20 ml culture of TB1 containing the eight pMAL plasmids ((pMAL-c2X, pIH1619 (carrying S146T) and pPR1610 (carrying A313V), each plasmid further containing a DNA encoding DHFR or GAPDH)) was grown to $2 \times 10^8$/ml in LB amp, induced with 0.3 mM IPTG, incubated for an additional two hours, then cells were harvested by centrifugation at 3000×g in a microfuge. Each pellet was resuspended in 2 ml of 50 mM Tris-Cl, pH 7.9, 50 mM NaCl, 0.75 mM EDTA, 0.6% Mega 10, 150 ug/ml lysozyme, and 20 Kunitz units/ml Serracia marscesens nuclease, and incubated at room temperature for 10 m. The resuspended pellet was designated the total cell extract. A sample of 125 ul was removed and centrifuged for 2 m at 14,000×g. The supernatant was removed and designated the soluble fraction. The pellet was resuspended in 125 ul of the same buffer, and designated the insoluble fraction. A sample (5 ul) of each fraction was run on SDS-PAGE for each strain (FIG. 5). The gels were dried and scanned, and the amount of MBP fusion protein in each lane was quantitated as a ratio of soluble protein to protein present in the cell lysate before centrifugation (Table 2). For both DHFR and GAPDH fusions, the A313V and S146T modified MBPs enhanced the solubility of the fusion protein as compared to wild-type MBP. Fusions made with the DM modified MBP, as expected, showed reduced solubility compared to wild-type MBP.

Example IV

Use of an MBP Mutant in *K. lactis*

Construction of a *K. lactis* MBP(A313V)-fusion Expression Vector

The gene encoding the mutant maltose-binding protein, MBP(A313V), was amplified by PCR using the forward and reverse primers, respectively:

oligo 23: 5' GCCCAAGCTTGCCACC ATGAAAATCGAAGAAGGT (SEQ ID NO:31) and oligo 24:

5' GCGCTCGAGCTTGTCATCGTCATCCGAGC TCGAATTAGTCTGCGC (SEQ ID NO:32). The forward primer was engineered to contain a HindIII restriction enzyme site (bold text) followed by the Kozak consensus sequence (italics) that immediately preceeds the malE gene initiation codon (underlined). The reverse primer was engineered to contain a XhoI restriction enzyme site (bold text) immediately followed by DNA encoding the proteolytic recognition site of the protease enterokinase (italic and underlined text). No stop codon was incorporated onto the reverse primer to allow for the construction of in-frame C-terminal MBP(A313V) fusion expression cassettes. The malE gene was amplified from the plasmid pPR1610 containing the full-length gene, using Phusion polymerase. The amplified gene was cloned into the HindIII and XhoI restriction sites of the *K. lactis* expression vector pKLAC1 to create a *K. lactis* MBP (A313V)-fusion expression vector (pKIMF2). This cloning strategy results in the replacement of the *K. lactis* α-mating factor pre-pro signal sequence in pKLAC1 with the malE gene. Thus the MBP- and MBP(A313V)-fusion proteins will not be directed to the secretory pathway but instead will be retained in the yeast cytosol.

Expression and Purification of an MBP(A313V)-Fusion Protein in *K. lactis*

The gene encoding a truncated form of paramyosin (Steel et al., *J. Immunol.* 145:3917-3923 (1990)) was amplified by PCR using the following primers:

oligo 25: 5'GCGCTCGAGAATTCCGCATTCGGTAG-TATG (SEQ ID NO:33) and oligo 26:

5'ATAAGAATGCGGCCGCTCACGACGTTGTAAAA CGACGGCCAGT (SEQ ID NO:34). The forward primer was engineered to contain a XhoI restriction site (bold text). The reverse primer was engineered to contain a NotI restriction site (bold text) immediately upstream of the PMΔSal stop codon (italic text).

The cloning strategy was as follows. The ~750 bp paramyosin gene was amplified and purified. The fragment was double-digested with XhoI and NotI and cloned into the XhoI and NotI restriction sites of the expression vector, pKIMF2 creating an in-frame fusion between the C-terminus and the N-terminus of PMΔSal. The plasmid constructed in this way was named pKLMF2-PMΔSal (FIG. 7).

The MBP(A313V)-PMΔSal fusion vector (pKIMF2-PMΔSal) was linearized by SacII restriction digestion and the purified product was transformed into chemically competent *K. lactis* cells using the *K. lactis* Protein Expression Kit according its instructions. Transformant colonies were selected on acetamide plates and clones containing the correctly integrated MBP(A313V)-PMΔSal expression cassette were identified by whole cell PCR as described in the above kit.

A 20 ml YPGalactose medium (1% yeast extract, 2% peptone, 2% galactose) culture was inoculated with a strain of *K. lactis* cells containing a multi-copy integrated MBP(A313V)-PMΔSal expression cassette and grown at 30° C. in an incubator with a shaking platform for 4 days. The total cell content of the culture after growth was determined to be approximately $8.2 \times 10^{10}$ cells (or approximately $4.1 \times 10^8$ cells/ml).

Cells were harvested by centrifugation at 8,000 rpm for 10 minutes at 4° C. The cells were washed once in distilled water to remove the excess media.

For the preparation of a lysate, the cells were re-suspended in a 2 ml solution of 10 mg/ml lyticase in 1M sorbitol and incubated at 37° C. for 1 hour. Cells were harvested by gentle centrifugation (7,000 r.p.m.) in a micro-centrifuge for 2 minutes. Cell pellets were resuspended in a total volume of 3 ml ice-cold amylose column buffer (20 mM Tris-Cl ph 7.4, 0.2 M NaCl, 1 mM EDTA) containing a protease inhibitor cocktail (Complete™ protease inhibitor cocktail, Roche). The cell slurry was transferred to a glass tube and placed on ice. An equal volume of acid washed glass beads (425-600 micron, Sigma) were added to the cell slurry and cells were broken by vortexing 10 times, each for a 1 minute duration. Cell lysate was transferred to a new tube and the glass beads washed 4 times with 1 ml column buffer. The cell lysate and washes were pooled and the cellular debris was removed by centrifugation. Cleared cell lysate was diluted to 8 ml with column buffer.

Figure 6:
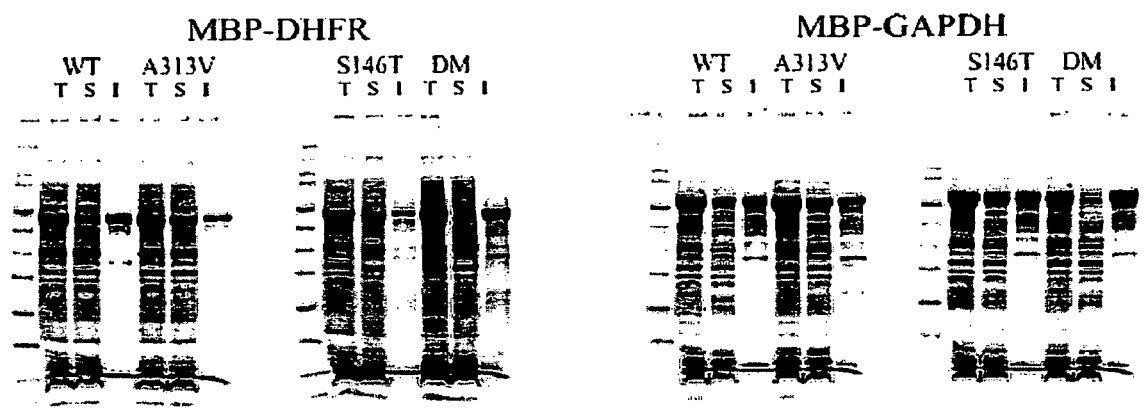
FIG. 6. SDS-PAGE gels showing the effect on solubility of fusing wild-type and modified MBPs to DHFR and GAPDH. DHFR fusion plasmids: WT=pIH1616; A313V=pIH1617; S146T=pIH1618; DM=pIH1646. GAPDH fusion plasmids: WT=pIH1625; A313V=pIH1626; S146T=pIH1627; DM=pIH1645. Lanes: T=total cell extract; S=soluble extract; I=resuspension of insoluble material. Equal portions of the indicated fraction were loaded in each lane. The ratio of soluble to insoluble protein was greater for both mutants compared with wild-type MBPs.
Figure 8:
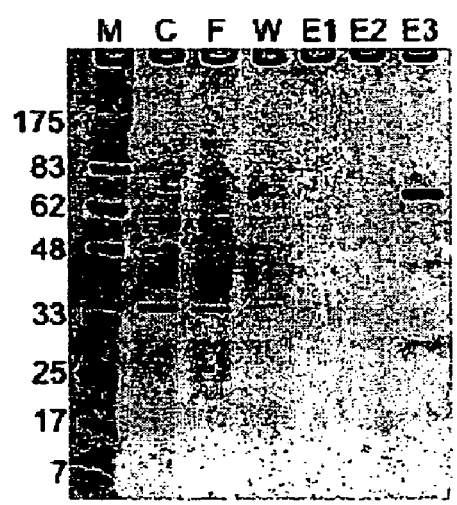
FIG. 8 shows fractions from the affinity purification, using an amylose resin column, of a fusion protein on an SDS-PAGE gel. An enhanced yield of modified MBP fusion protein was produced by expressing MBP (A313V)PMΔSal in *Kluyveromyces lactis* cells carrying an MBP (A313v)-PMΔ-Sal expression cassette.

For fusion protein purification, the cell lysate was passed over a 1.6 ml amylose resin column pre-equilibrated with 15 ml of column buffer. The column was washed with 24 ml of column buffer and bound protein was eluted in 0.4 ml fractions with column buffer containing 10 mM maltose. Cell lysate and purified proteins were resolved by SDS-PAGE on a 10-20% Tris-Glycine gradient gel. Proteins were identified by SimplyBlue Safestain. FIG. 6 shows that the major eluted protein corresponds to the size expected (68.5 kDa) for an MBP(A313V)-PMΔSal fusion protein.

TABLE 1

Yield of MBP-Klenow for wild-type and modified MBP's

| plasmid | MBP | Yield |
|---|---|---|
| pIH1062 | WT | 0.7 mgs |
| pIH1643 | A313V | 2 mgs |
| pIH1644 | S146T | 0.7 mgs |

TABLE 2

Yield of MBP-CBD for wild-type and MBP(A313V)

| plasmid | MBP | Yield |
|---|---|---|
| pMB50 | WT | 13.2 mgs |
| pIH1660 | A313V | 21.8 mgs |

TABLE 3

Solubility of MBP fusion proteins

| Plasmid | Fusion protein | % Soluble |
|---|---|---|
| pIH1616 | MBP-DHFR | 36% |
| pIH1617 | MBP(A313V)-DHFR | 67% |
| pIH1618 | MBP(S146T)-DHFR | 67% |
| pIH1646 | MBP(DM)-DHFR | 25% |
| pIH1625 | MBP-GAPDH | 42% |
| pIH1626 | MBP(A313V)-GAPDH | 59% |
| pIH1627 | MBP(S146T)-GAPDH | 53% |
| pIH1645 | MBP(DM)-GAPDH | 17% |

SEQUENCE LISTING

<160> NUMBER OF SEQ ID NOS: 34

<210> SEQ ID NO 1
<211> LENGTH: 1188
<212> TYPE: DNA
<213> ORGANISM: unknown
<220> FEATURE:
<223> OTHER INFORMATION: DNA encoding wild-type maltose binding protein

<400> SEQUENCE: 1

```
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta taacaaagat ctgctgccga cccgccaaa aacctgggaa      420 gagatcccgg cgctggataa agaactgaaa gcgaaggta gagcgcgct gatgttcaac      480 ctgcaagaac cgtacttcac ctggccgctg attgctgctg acggggtta tgcgttcaag     540 tatgaaaacg gcaagtacga cattaaagac gtgggcgtgg ataacgctgg cgcgaaagcg     600
ggtctgacct tcctggttga cctgattaaa aacaaacaca tgaatgcaga caccgattac     660
tccatcgcag aagctgcctt taataaaggc gaaacagcga tgaccatcaa cggcccgtgg     720
```

```
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta ataaagacaa accgctgggt gccgtagcgc tgaagtctta cgaggaagag    960
ttggcgaaag atccacgtat tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctcg   1140
aacaacaaca acaataacaa taacaacaac ctcgggatcg agggaagg               1188
```

<210> SEQ ID NO 2
<211> LENGTH: 136
<212> TYPE: PRT
<213> ORGANISM: unknown
<220> FEATURE:
<223> OTHER INFORMATION: wild-type maltose binding protein

<400> SEQUENCE: 2

```
Leu Glu Arg Trp Glu Ile Ser Glu Glu Lys Leu Thr Asp Leu Val Asp
 1               5                  10                  15

Lys Asn Pro Ser Leu Arg Gly Met Ile Leu Gly Tyr Val Ala Glu Asp
            20                  25                  30

Lys Phe His Glu Leu Phe Leu Glu Asp Glu Arg Val Lys Glu Val Ser
        35                  40                  45

Lys Asp Asp Asp His Asp Arg Lys Lys Gly Asp Arg Thr Phe Ile
    50                  55                  60

Tyr Lys Gly Lys Lys Phe Thr Val Glu Val Lys Ser Leu Gln Thr Ala
65                  70                  75                  80

Met Cys Lys Lys Asn Glu Asp Gly Thr Tyr Ser Gly Lys Ala Gln Val
                85                  90                  95

Asp Gly Ser Asp Arg Arg Ile Val Lys Phe Pro Asp Asn Ser Glu Leu
            100                 105                 110

Asn Thr Thr Leu Leu Leu Lys Gly Glu Phe Asp Leu Leu Ala Val Asn
        115                 120                 125

Cys Phe Ala Phe Gly Glu Gly Trp
    130                 135
```

<210> SEQ ID NO 3
<211> LENGTH: 1188
<212> TYPE: DNA
<213> ORGANISM: unknown
<220> FEATURE:
<223> OTHER INFORMATION: DNA sequence encoding the maltose binding
      protein mutant A9

<400> SEQUENCE: 3

```
gcacttcacc aacaaggacc atagcatatg aaaatcgaag aaggtaaact ggtaatctgg     60
attaacggcg ataaaggcta tagcggtctc gctgaagtcg gtaagaaatt cgagaaagat    120
accggaatta aagtcaccgt tgagcatccg gataaactgg aagagaaatt cccacaggtt    180
gcggcaactg gcgatggccc tgacattatc ttctgggcac acgaccgctt tggtggctac    240
gctcaatctg gcctgttggc tgaaatcacc ccggacaaag cgttccagga caagctgtat    300
ccgtttacct gggatgccgt acgttacaac ggcaagctga ttgcttaccc gatcgctgtt    360
gaagcgttat cgctgattta taacaaagat ctgctgccga accgccaaaa acctgggaa    420 gagatcccgg cgctggataa agaactgaaa gcgaaaggta gagcgcgct gatgttcaac    480
```

-continued

```
ctgcaagaac cgtacttcac ctggccgctg attgctgctg acggggggtta tgcgttcaag    540 tatgaaaacg gcaagtacga cattaaagac gtgggcgtgg ataacgctgg cgcgaaagcg    600
ggtctgacct tcctggttga cctgattaag aacaaacaca tgaatgcaga caccgattac    660
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta ataaagacga accgctgggt gccgtagcgc tgaagtctta cgaggaagag    960
ttggtgaaag atccacgtat tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctcg   1140
aacaacaaca acaataacaa taacaacaac ctcgggatcg agggaagg              1188
```

<210> SEQ ID NO 4
<211> LENGTH: 387
<212> TYPE: PRT
<213> ORGANISM: unknown
<220> FEATURE:
<223> OTHER INFORMATION: maltose binding protein mutant A9

<400> SEQUENCE: 4

```
Met Lys Ile Glu Glu Gly Lys Leu Val Ile Trp Ile Asn Gly Asp Lys
1               5                   10                  15

Gly Tyr Ser Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240
```

```
Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Glu Pro Leu Gly Ala Val Ala
    290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385

<210> SEQ ID NO 5
<211> LENGTH: 1188
<212> TYPE: DNA
<213> ORGANISM: unknown
<220> FEATURE:
<223> OTHER INFORMATION: DNA sequence encoding the maltose binding
      protein mutant G8-1

<400> SEQUENCE: 5
gcacttcacc aacaaggacc atagcatatg aaaatcgaag aaggtaaaact ggtaatctgg      60 attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg cgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta taacaaagat ctgctgccga accgccaaa acctgggaa      420 gagatcccgg cgctggataa agaactgaaa gcgaaaggta agaccgcgct gatgttcaac     480
ctgcaagaac cgtacttcac ctggccgctg attgctgctg acgggggcta tgcgttcaag     540
tatgaaaacg gcaagtacga cattaaagac gtgggcgtgg ataacgctgg cgcgaaagcg     600
ggtctgacct tcctggttga cctgattaaa acaaacacat gaatgcaga caccgattac     660 tccatcgcag aagctgcctt taataaaggc gaaacagcg tgaccatcaa cggcccgtgg     720
gcatggtcca acatcgacac cagcaaagtg aattatggtg taacggtact gccgaccttc     780
aagggtcaac catccaaacc gttcgttggc gtgctgagcg caggtattaa cgccgccagt     840
ccgaacaaag agctggcaaa agagttcctc gaaaactatc tgctgactga tgaaggtctg     900
gaagcggtta ataaagacaa accgctgggt gccgtagcgc tgaagtctta cgaggaagag     960
ttggcgaaag atccacgtat tgccgccact atggaaaacg cccagaaagg tgaaatcatg    1020
ccgaacatcc cgcagatgtc cgctttctgg tatgccgtgc gtactgcggt gatcaacgcc    1080
gccagcggtc gtcagactgt cgatgaagcc ctgaaagacg cgcagactaa ttcgagctcg    1140
```

-continued aacaacaaca acaataacaa taacaacaac ctcgggatcg agggaagg  1188

<210> SEQ ID NO 6
<211> LENGTH: 387
<212> TYPE: PRT
<213> ORGANISM: unknown
<220> FEATURE:
<223> OTHER INFORMATION: maltose binding protein mutant G8-1

<400> SEQUENCE: 6

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Thr Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350
```

```
Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385

<210> SEQ ID NO 7
<211> LENGTH: 6835
<212> TYPE: DNA
<213> ORGANISM: unknown
<220> FEATURE:
<223> OTHER INFORMATION: pMB50

<400> SEQUENCE: 7
```

| | | | | | |
|---|---|---|---|---|---|
| ccgacaccat | cgaatggtgc | aaaacctttc | gcggtatggc | atgatagcgc | ccggaagaga | 60 |
| gtcaattcag | ggtggtgaat | gtgaaaccag | taacgttata | cgatgtcgca | gagtatgccg | 120 |
| gtgtctctta | tcagaccgtt | tcccgcgtgg | tgaaccaggc | cagccacgtt | tctgcgaaaa | 180 |
| cgcgggaaaa | agtggaagcg | gcgatggcgg | agctgaatta | cattcccaac | cgcgtggcac | 240 |
| aacaactggc | gggcaaacag | tcgttgctga | ttggcgttgc | cacctccagt | ctggccctgc | 300 |
| acgcgccgtc | gcaaattgtc | gcggcgatta | aatctcgcgc | cgatcaactg | ggtgccagcg | 360 |
| tggtggtgtc | gatggtagaa | cgaagcggcg | tcgaagcctg | taaagcggcg | gtgcacaatc | 420 |
| ttctcgcgca | acgcgtcagt | gggctgatca | ttaactatcc | gctggatgac | caggatgcca | 480 |
| ttgctgtgga | agctgcctgc | actaatgttc | cggcgttatt | tcttgatgtc | tctgaccaga | 540 |
| cacccatcaa | cagtattatt | ttctcccatg | aagacggtac | gcgactgggc | gtggagcatc | 600 |
| tggtcgcatt | gggtcaccag | caaatcgcgc | tgttagcggg | cccattaagt | tctgtctcgg | 660 |
| cgcgtctgcg | tctggctggc | tggcataaat | atctcactcg | caatcaaatt | cagccgatag | 720 |
| cggaacggga | aggcgactgg | agtgccatgt | ccggttttca | acaaaccatg | caaatgctga | 780 |
| atgagggcat | cgttcccact | gcgatgctgg | ttgccaacga | tcagatggcg | ctgggcgcaa | 840 |
| tgcgcgccat | taccgagtcc | gggctgcgcg | ttggtgcgga | tatctcggta | gtgggatacg | 900 |
| acgataccga | agacagctca | tgttatatcc | cgccgttaac | caccatcaaa | caggattttc | 960 |
| gcctgctggg | gcaaaccagc | gtggaccgct | tgctgcaact | ctctcagggc | caggcggtga | 1020 |
| agggcaatca | gctgttgccc | gtctcactgg | tgaaaagaaa | aaccaccctg | gcgcccaata | 1080 |
| cgcaaaccgc | ctctccccgc | gcgttggccg | attcattaat | gcagctggca | cgacaggttt | 1140 |
| cccgactgga | aagcgggcag | tgagcgcaac | gcaattaatg | tgagttagct | cactcattag | 1200 |
| gcacaattct | catgtttgac | agcttatcat | cgactgcacg | gtgcaccaat | gcttctggcg | 1260 |
| tcaggcagcc | atcggaagct | gtggtatggc | tgtgcaggtc | gtaaatcact | gcataattcg | 1320 |
| tgtcgctcaa | ggcgcactcc | cgttctggat | aatgttttt | cgccgacat | cataacggtt | 1380 |
| ctggcaaata | ttctgaaatg | agctgttgac | aattaatcat | cggctcgtat | aatgtgtgga | 1440 |
| attgtgagcg | gataacaatt | tcacacagga | aacagccagt | ccgtttaggt | gttttcacga | 1500 |
| gcacttcacc | aacaaggacc | atagattatg | aaaatcgaag | aaggtaaact | ggtaatctgg | 1560 |
| attaacggcg | ataaaggcta | taacggtctc | gctgaagtcg | gtaagaaatt | cgagaaagat | 1620 |
| accggaatta | aagtcaccgt | tgagcatccg | gataaactgg | aagagaaatt | cccacaggtt | 1680 |
| gcggcaactg | gcgatgggcc | tgacattatc | ttctgggcac | acgaccgctt | ggtggctac | 1740 |
| gctcaatctg | gcctgttggc | tgaaatcacc | ccggacaaag | cgttccagga | caagctgtat | 1800 |

```
ccgtttacct gggatgccgt acgttacaac ggcaagctga ttgcttaccc gatcgctgtt    1860
gaagcgttat cgctgattta taacaaagat ctgctgccga acccgccaaa aacctgggaa    1920
gagatcccgg cgctggataa agaactgaaa gcgaaaggta agagcgcgct gatgttcaac    1980
ctgcaagaac cgtacttcac ctggccgctg attgctgctg acgggggtta tgcgttcaag    2040
tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc gcagatgtc cgcttctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaagggg tacgctcgag    2700
ggttctcagc atgcaccggg tggcctgacc ggtctgaact caggcctcac gacaaatcct    2760
ggtgtatccg cttggcaggt caacacagct tatactgcgg acaattggt cacatataac    2820 ggcaagacgt ataaatgttt gcagccccac acctccttgg caggatggga accatccaac    2880
gttcctgcct tgtggcagct tcaatgactg caggcaagct tggcactggc cgtcgtttta    2940
caacgtcgtg actgggaaaa ccctggcgtt acccaactta atcgccttgc agcacatccc    3000
cctttcgcca gctggcgtaa tagcgaagag gcccgcaccg atcgccttc ccaacagttg    3060 cgcagcctga atggcgaatg gcagcttggc tgttttggcg gatgagataa gatttttcagc    3120 ctgatacaga ttaaatcaga acgcagaagc ggtctgataa aacagaattt gcctggcggc    3180
agtagcgcgg tggtcccacc tgaccccatg ccgaactcag aagtgaaacg ccgtagcgcc    3240
gatggtagtg tggggtctcc ccatgcgaga gtagggaact gccaggcatc aaataaaacg    3300
aaaggctcag tcgaaagact gggcctttcg ttttatctgt tgtttgtcgg tgaacgctct    3360
cctgagtagg acaaatccgc cgggagcgga tttgaacgtt gcgaagcaac ggcccggagg    3420
gtggcgggca ggacgcccgc cataaactgc caggcatcaa attaagcaga aggccatcct    3480
gacggatggc cttttgcgt tctacaaac tcttttgtt tattttcta aatacattca    3540 aatatgtatc cgctcatgag acaataaccc tgataaatgc ttcaataata ttgaaaagg    3600 aagagtatga gtattcaaca tttccgtgtc gcccttattc cctttttgc ggcattttgc    3660 cttcctgttt ttgctcaccc agaaacgctg gtgaaagtaa agatgctga agatcagttg    3720 ggtgcacgag tgggttacat cgaactggat ctcaacagcg gtaagatcct tgagagtttt    3780
cgccccgaag aacgttctcc aatgatgagc acttttaaag ttctgctatg tggcgcggta    3840
ttatcccgtg ttgacgccgg gcaagagcaa ctcggtcgcc gcatacacta ttctcagaat    3900
gacttggttg agtactcacc agtcacagaa aagcatctta cggatggcat gacagtaaga    3960
gaattatgca gtgctgccat aaccatgagt gataacactg cggccaactt acttctgaca    4020
acgatcggag gaccgaagga gctaaccgct ttttgcaca acatggggga tcatgtaact    4080
cgccttgatc gttgggaacc ggagctgaat gaagccatac caaacgacga gcgtgacacc    4140
acgatgcctg tagcaatggc aacaacgttg cgcaaactat taactggcga actacttact    4200
```

```
ctagcttccc ggcaacaatt aatagactgg atggaggcgg ataaagttgc aggaccactt    4260
ctgcgctcgg cccttccggc tggctggttt attgctgata atctggagc cggtgagcgt     4320 gggtctcgcg gtatcattgc agcactgggg ccagatggta agccctcccg tatcgtagtt    4380
atctacacga cggggagtca ggcaactatg gatgaacgaa atagacagat cgctgagata    4440
ggtgcctcac tgattaagca ttggtaactg tcagaccaag tttactcata tatactttag    4500
attgatttac cccggttgat aatcagaaaa gccccaaaaa caggaagatt gtataagcaa    4560
atatttaaat tgtaaacgtt aatattttgt taaaattcgc gttaaatttt tgttaaatca    4620
gctcattttt taaccaatag gccgaaatcg gcaaaatccc ttataaatca aaagaatagc    4680
ccgagatagg gttgagtgtt gttccagttt ggaacaagag tccactatta agaacgtgg     4740 actccaacgt caaagggcga aaaccgtct atcagggcga tggcccacta cgtgaaccat     4800
cacccaaatc aagttttttg gggtcgaggt gccgtaaagc actaaatcgg aaccctaaag    4860
ggagcccccg atttagagct tgacggggaa agccggcgaa cgtggcgaga aaggaaggga    4920
agaaagcgaa aggagcgggc gctagggcgc tggcaagtgt agcggtcacg ctgcgcgtaa    4980
ccaccacacc cgccgcgctt aatgcgccgc tacagggcgc gtaaaaggat ctaggtgaag    5040
atcctttttg ataatctcat gaccaaaatc ccttaacgtg agttttcgtt ccactgagcg    5100
tcagaccccg tagaaaagat caaggatct tcttgagatc cttttttttct gcgcgtaatc    5160 tgctgcttgc aaacaaaaaa accaccgcta ccagcggtgg tttgtttgcc ggatcaagag    5220
ctaccaactc tttttccgaa ggtaactggc ttcagcagag cgcagatacc aaatactgtc    5280
cttctagtgt agccgtagtt aggccaccac ttcaagaact ctgtagcacc gcctacatac    5340
ctcgctctgc taatcctgtt accagtggct gctgccagtg cgataagtc gtgtcttacc     5400 gggttggact caagacgata gttaccggat aaggcgcagc ggtcgggctg aacgggggt     5460 tcgtgcacac agcccagctt ggagcgaacg acctacaccg aactgagata cctacagcgt    5520
gagctatgag aaagcgccac gcttcccgaa gggagaaagg cggacaggta tccggtaagc    5580
ggcagggtcg gaacaggaga gcgcacgagg gagcttccag ggggaaacgc ctggtatctt    5640
tatagtcctg tcgggtttcg ccacctctga cttgagcgtc gatttttgtg atgctcgtca    5700
ggggggcgga gcctatggaa aaacgccagc aacgcggcct ttttacggtt cctggccttt    5760
tgctggcctt ttgctcacat gttctttcct gcgttatccc ctgattctgt ggataaccgt    5820
attaccgcct ttgagtgagc tgataccgct cgccgcagcc gaacgaccga gcgcagcgag    5880
tcagtgagcg aggaagcgga agagcgcctg atgcggtatt ttctccttac gcatctgtgc    5940
ggtatttcac accgcatatg gtgcactctc agtacaatct gctctgatgc cgcatagtta    6000
agccagtata cactccgcta tcgctacgtg actgggtcat ggctgcgccc cgacacccgc    6060
caacacccgc tgacgcgccc tgacgggctt gtctgctccc ggcatccgct tacagacaag    6120
ctgtgaccgt ctccgggagc tgcatgtgtc agaggttttc accgtcatca ccgaaacgcg    6180
cgaggcagct gcggtaaagc tcatcagcgt ggtcgtgcag cgattcacag atgtctgcct    6240
gttcatccgc gtccagctcg ttgagtttct ccagaagcgt taatgtctgg cttctgataa    6300
agcgggccat gttaagggcg gttttttcct gtttggtcac ttgatgcctc cgtgtaaggg    6360
ggaatttctg ttcatggggg taatgatacc gatgaaacga gagaggatgc tcacgatacg    6420
ggttactgat gatgaacatg cccggttact ggaacgttgt gagggtaaac aactggcggt    6480
atggatgcgg cgggaccaga gaaaaatcac tcagggtcaa tgccagcgct tcgttaatac    6540
```

```
agatgtaggt gttccacagg gtagccagca gcatcctgcg atgcagatcc ggaacataat    6600
ggtgcagggc gctgacttcc gcgtttccag actttacgaa acacggaaac cgaagaccat    6660
tcatgttgtt gctcaggtcg cagacgtttt gcagcagcag tcgcttcacg ttcgctcgcg    6720
tatcggtgat tcattctgct aaccagtaag gcaaccccgc cagcctagcc gggtcctcaa    6780
cgacaggagc acgatcatgc gcaccgtggg ccaggaccca cgctgcccg aaatt          6835

<210> SEQ ID NO 8
<211> LENGTH: 10632
<212> TYPE: DNA
<213> ORGANISM: unknown
<220> FEATURE:
<223> OTHER INFORMATION: pKLIMF2-PMdeltaSal

<400> SEQUENCE: 8
aagcttgcca ccatgaaaat cgaagaaggt aaactggtaa tctggattaa cggcgataaa      60
ggctataacg gtctcgctga agtcggtaag aaattcgaga agataccgg aattaaagtc     120 accgttgagc atccggataa actggaagag aaattcccac aggttgcggc aactggcgat    180
ggccctgaca ttatcttctg gcacacgac cgctttggtg gctacgctca atctggcctg     240
ttggctgaaa tcaccccgga caaagcgttc caggacaagc tgtatccgtt tacctgggat    300
gccgtacgtt acaacggcaa gctgattgct tacccgatcg ctgttgaagc gttatcgctg    360
atttataaca agatctgct gccgaacccg ccaaaaacct gggaagagat cccggcgctg     420
gataaagaac tgaaagcgaa aggtaagagc gcgctgatgt tcaacctgca agaaccgtac    480
ttcacctggc cgctgattgc tgctgacggg ggttatgcgt tcaagtatga aaacggcaag    540
tacgacatta agacgtggg cgtggataac gctggcgcga aagcgggtct gaccttcctg    600
gttgacctga ttaaaaacaa acacatgaat gcagacaccg attactccat cgcagaagct    660
gcctttaata aaggcgaaac agcgatgacc atcaacggcc cgtgggcatg gtccaacatc    720
gacaccagca agtgaatta tggtgtaacg gtactgccga ccttcaaggg tcaaccatcc    780
aaaccgttcg ttggcgtgct gagcgcaggt attaacgccg ccagtccgaa caaagagctg    840
gcaaaagagt tcctcgaaaa ctatctgctg actgatgaag gtctggaagc ggttaataaa    900
gacaaaccgc tgggtgccgt agcgctgaag tcttacgagg aagagttggt gaaagatcca    960
cgtattgccg ccactatgga aaacgcccag aaaggtgaaa tcatgccgaa catcccgcag   1020
atgtccgctt tctggtatgc cgtgcgtact gcggtgatca acgccgccag cggtcgtcag   1080
actgtcgatg aagcccctgaa agacgcgcag actaattcga gctcggatga cgatgacaag   1140
ctcgagaatt ccgcattcgg tagtatgtcg gttgccgatt tgggaagttt aactcgcttg   1200
gaggacaaga ttcgtctact gcaagaagat ctcgaatccg aacgtgaact tcgaaataga   1260
atcgaacgag aaagagctga tcttagtgta caactgattg cattaactga tagacttgaa   1320
gatgctgagg tactactga tagtcagatt gaatcaaatc gtaaacgtga agcagaattg    1380
caaaaattac gtaaattatt ggaagaatca caattagaaa atgaagatgc aatgaatgtt   1440
ttacgtaaaa agcatcaaga tgcatgtctc gattacgctg aacaaattga acaattacaa   1500
aagaaaaatt caaagattga tcgtgaacgt caacgtctgc aacatgaagt aattgagctt   1560
actgcgacaa ttgatcaact tcaaaaggat aagcatttgg cggaaaaagc agcggaacgt   1620
tttgaagcgc aaactatcga attgagtaat aaagttgaag atttaaatcg acatgttaat   1680
gatttagctc aacaacgtca acgtttacaa gctgaaaata cgatcttct caaagagatt   1740 catgatcaaa aagtacaatt ggataatttg caacacgtga atatcaact tgcgcaacaa   1800
```

```
cttgaagaag cacgtcgacc tgcaggcaag cttggcactg gccgtcgttt tacaacgtcg   1860
tgagcggccg cttaattaag gccttgaatc gagaatttat acttagataa gtatgtactt   1920
acaggtatat ttctatgaga tactgatgta tacatgcatg ataatattta aacggttatt   1980
agtgccgatt gtcttgtgcg ataatgacgt tcctatcaaa gcaatacact taccacctat   2040
tacatgggcc aagaaaatat tttcgaactt gtttagaata ttagcacaga gtatatgatg   2100
atatccgtta gattatgcat gattcattcc tacaactttt tcgtagcata aggattaatt   2160
acttggatgc aataaaaaaa aaaaaacatc gagaaaattt cagcatgctc agaaacaatt   2220
gcagtgtatc aaagtaaaaa aaagattttc actacatgtt cctttgaag aaagaaaatc    2280
atggaacatt agatttacaa aaatttaacc accgctgatt aacgattaga ccgttaagcg   2340
cacaacaggt tattagtaca gagaaagcat tctgtggtgt tgccccggac tttcttttgc   2400
gacataggta aatcgaatac catcatacta tcttttccaa tgactcccta agaaagact    2460
cttcttcgat gttgtatacg ttggagcata gggcaagaat tgtggcttga gatcatcctt   2520
ttgttgtttc cgggtgtaca atatggactt cctctttct ggcaaccaaa cccatacatc     2580
gggattccta taatacctc gttggtctcc ctaacatgta ggtggcggag ggagatata     2640
caatagaaca gataccagac aagacataat gggctaaaca agactacacc aattacactg   2700
cctcattgat ggtggtacat aacgaactaa tactgtagcc ctagacttga tagccatcat   2760
catatcgaag tttcactacc ctttttccat ttgccatcta ttgaagtaat aataggcgca   2820
tgcaacttct ttctttttt tttcttttct ctctccccg ttgttgtctc accatatccg     2880
caatgacaaa aaaatgatgg aagacactaa aggaaaaat taacgacaaa gacagcacca    2940
acagatgtcg ttgttccaga gctgatgagg ggtatctcga agcacacgaa actttttcct   3000
tccttcattc acgcacacta ctctctaatg agcaacggta tacggccttc cttccagtta   3060
cttgaatttg aaataaaaaa aagtttgctg tcttgctatc aagtataaat agacctgcaa   3120
ttattaatct tttgtttcct cgtcattgtt ctcgttccct ttcttccttg tttcttttc    3180
tgcacaatat ttcaagctat accaagcata caatcaagga attccggatc cgccaccatg   3240
cctcaatcct gggaagaact ggccgctgat aagcgcgccc gcctcgcaaa aaccatccct   3300
gatgaatgga agtccagac gctgcctgcg aagacagcg ttattgattt cccaaagaaa     3360
tcggggatcc tttcagaggc cgaactgaag atcacagagg cttccgctgc ggatcttgtg   3420
tccaagctgg cggccggaga gttgacctcg gtggaagtta cgctagcatt ctgtaaacgg   3480
gcagcaatcg cccagcagtt aacaaactgc gcccacgagt tcttccctga cgccgctctc   3540
gcgcaggcaa gggaactcga tgaatactac gcaaagcaca agagacccgt tggtccactc   3600
catggcctcc ccatctctct caaagaccag cttcgagtca agggctacga aacatcaatg   3660
ggctacatct catggctaaa caagtacgac gaagggact cggttctgac aaccatgctc     3720
cgcaaagccg gtgccgtctt ctacgtcaag acctctgtcc cgcagaccct gatggtctgc   3780
gagacagtca acaacatcat cgggcgcacc gtcaacccac gcaacaagaa ctggtcgtgc   3840
ggcggcagtt ctggtggtga gggtgcgatc gttgggattc gtgtggcgt catcggtgta    3900
ggaacggata tcggtggctc gattcgagtg ccggccgcgt tcaacttcct gtacggtcta   3960
aggccgagtc atgggcggct gccgtatgca aagatgcgca acagcatgga gggtcaggag   4020
acggtgcaca cgttgtcgg gccgattacg cactctgttg aggacctccg cctcttcacc   4080
aaatccgtcc tcggtcagga gccatggaaa tacgactcca aggtcatccc catgccctgg   4140
```

```
cgccagtccg agtcggacat tattgcctcc aagatcaaga acggcgggct caatatcggc    4200
tactacaact tcgacggcaa tgtccttcca caccctccta cctgcgcgg cgtggaaact     4260
accgtcgccg cactcgccaa agccggtcac accgtgaccc cgtggacgcc atacaagcac    4320
gatttcggcc acgatctcat ctcccatatc tacgcggctg acggcagcgc cgacgtaatg    4380
cgcgatatca gtgcatccgg cgagccggcg attccaaata tcaaagacct actgaacccg    4440
aacatcaaag ctgttaacat gaacgagctc tgggacacgc atctccagaa gtggaattac    4500
cagatggagt accttgagaa atggcgggag gctgaagaaa aggccgggaa ggaactggac    4560
gccatcatcg cgccgattac gcctaccgct gcggtacggc atgaccagtt ccggtactat    4620
gggtatgcct ctgtgatcaa cctgctggat ttcacgagcg tggttgttcc ggttaccttt    4680
gcggataaga acatcgataa gaagaatgag agtttcaagg cggttagtga gcttgatgcc    4740
ctcgtgcagg aagagtatga tccggaggcg taccatgggg caccggttgc agtgcaggtt    4800
atcggacgga gactcagtga agagaggacg ttggcgattg cagaggaagt ggggaagttg    4860
ctgggaaatg tggtgactcc atagcccggg gggggctcga tcccctcgcg agttggttca    4920
gctgctgcct gaggctggac gacctcgcgg agttctaccg gcagtgcaaa tccgtcggca    4980
tccaggaaac cagcagcggc tatccgcgca tccatgcccc cgaactgcag gagtggggag    5040
gcacgatggc cgctttggtc gatctagatt acgtggaaga aaggtagtaa aagtagtagt    5100
ataagtagta aaagaggta aaagagaaa accggctaca tactagagaa gcacgtacac     5160
aaaaactcat aggcacttca tcatacgaca gtttcttgat gcattataat agtgtattag    5220
atattttcag aaatatgcat agaacctcct cttgccttta cttttttatac atagaacatt   5280
ggcagattta cttacactac tttgtttcta cgccatttct tttgttttca cacttagac    5340
aagttgttga gaaccggact actaaaaagc aatgttccca ctgaaaatca tgtacctgca    5400
ggataataac cccctaattc tgcatcgatc cagtatgttt ttttttctct actcattttt    5460
acctgaagat agagcttcta aaacaaaaaa aatcagtgat tacatgcata ttgtgtgttc    5520
tagtaaccaa aggaaaggaa cagatagata aaattccgag actgtcaaat taggtttttt    5580
tcttttttt tggcgggagt cagtgggccg aaatatgttc ttggcctaga acttaatctg     5640
gtttgatcat gccaatactt gcctgagtgc ccgacttttt gcccaccctc ttgccttctg    5700
tcatccttca aaacccacct gttttccagc cgtatcttcg ctcgcatcta cacatactgt    5760
gccatatctt gtgtgtagcc ggacgtgact atgaccaaaa acaaacaagg agaactgttc    5820
gccgatttgt aacactcctg catccatcca agtgggtatg cgctatgcaa tgttaagcta    5880
ggtcaggtca gaccaggtcc aaggacagca acttgactgt atgcaacctt taccatcttt    5940
gcacagaaca tacttgtagc tagctagtta cacttatgga ccgaaaaggc accccaccat    6000
gtctgtccgg ctttagagta cggccgcaga ccgctgattt gccttgccaa gcagtagtca    6060
caatgcatcg catgagcaca cgggcacggg cacgggcaca ggaaccattg caaaaatac    6120
cagatacact ataccgacgt atatcaagcc caagtttaaa attcctaaat ttccgcggct    6180
acttttcaat tccctatagt gagtcgtatt aaattcgtaa tcatgtcata gctgtttcct    6240
gtgtgaaatt gttatccgct cacaattcca cacaacatac gagccggaag cataaagtgt    6300
aaagcctggg gtgcctaatg agtgagctaa ctcacattaa ttgcgttgcg ctcactgccc    6360
gctttccagt cgggaaacct gtcgtgccag ctgcattaat gaatcggcca acgcgcgggg    6420
agaggcggtt tgcgtattgg cgctcttccg cttcctcgc tcactgactc gctgcgctcg     6480
gtcgttcggc tgcggcgagc ggtatcagct cactcaaagg cggtaatacg ttatccaca    6540
```

```
gaatcagggg ataacgcagg aaagaacatg tgagcaaaag gccagcaaaa ggccaggaac    6600
cgtaaaaagg ccgcgttgct ggcgttttc ataggctcc gcccctga cgagcatcac    6660 aaaaatcgac gctcaagtca gaggtggcga acccgacag gactataaag ataccaggcg    6720
tttccccctg gaagctccct cgtgcgctct cctgttccga ccctgccgct taccggatac    6780
ctgtccgcct ttctcccttc gggaagcgtg gcgctttctc atagctcacg ctgtaggtat    6840
ctcagttcgg tgtaggtcgt tcgctccaag ctgggctgtg tgcacgaacc ccccgttcag    6900
cccgaccgct gcgccttatc cggtaactat cgtcttgagt ccaacccggt aagacacgac    6960
ttatcgccac tggcagcagc cactggtaac aggattagca gagcgaggta tgtaggcggt    7020
gctacagagt tcttgaagtg gtggcctaac tacggctaca ctagaagaac agtatttggt    7080
atctgcgctc tgctgaagcc agttaccttc ggaaaaagag ttggtagctc ttgatccggc    7140
aaacaaacca ccgctggtag cggtggtttt tttgtttgca agcagcagat tacgcgcaga    7200 aaaaaggat ctcaagaaga tcctttgatc ttttctacgg ggtctgacgc tcagtggaac    7260
gaaaactcac gttaagggat tttggtcatg agattatcaa aaaggatctt cacctagatc    7320
cttttaaatt aaaaatgaag ttttaaatca atctaaagta tatatgagta aacttggtct    7380
gacagttacc aatgcttaat cagtgaggca cctatctcag cgatctgtct atttcgttca    7440
tccatagttg cctgactccc cgtcgtgtag ataactacga tacgggaggg cttaccatct    7500
ggccccagtg ctgcaatgat accgcgagac ccacgctcac cggctccaga tttatcagca    7560
ataaaccagc cagccggaag ggccgagcgc agaagtggtc ctgcaacttt atccgcctcc    7620
atccagtcta ttaattgttg ccgggaagct agagtaagta gttcgccagt taatagtttg    7680
cgcaacgttg ttgccattgc tacaggcatc gtggtgtcac gctcgtcgtt tggtatggct    7740
tcattcagct ccggttccca acgatcaagg cgagttacat gatcccccat gttgtgcaaa    7800
aaagcggtta gctccttcgg tcctccgatc gttgtcagaa gtaagttggc cgcagtgtta    7860
tcactcatgg ttatggcagc actgcataat tctcttactg tcatgccatc cgtaagatgc    7920
ttttctgtga ctggtgagta ctcaaccaag tcattctgag aatagtgtat gcggcgaccg    7980
agttgctctt gcccggcgtc aatacgggat aataccgcgc cacatagcag aactttaaaa    8040
gtgctcatca ttggaaaacg ttcttcgggg cgaaaactct caaggatctt accgctgttg    8100
agatccagtt cgatgtaacc cactcgtgca cccaactgat cttcagcatc ttttactttc    8160
accagcgttt ctgggtgagc aaaaacagga aggcaaaatg ccgcaaaaaa gggaataagg    8220
gcgacacgga aatgttgaat actcatactc ttcctttttc aatattattg aagcatttat    8280
cagggttatt gtctcatgag cggatacata tttgaatgta tttagaaaaa taaacaaata    8340
ggggttccgc gcacatttcc ccgaaaagtg ccacctgacg cgccctgtag cggcgcatta    8400
agcgcggcgg gtgtggtggt tacgcgcagc gtgaccgcta cacttgccag cgccctagcg    8460
cccgctcctt tcgctttctt cccttccttt ctcgccacgt tcgccggctt tccccgtcaa    8520
gctctaaatc gggggctccc tttagggttc cgatttagtg ctttacgca cctcgacccc    8580 aaaaaacttg attagggtga tggttcacgt agtgggccat cgccctgata cggtttttt    8640 cgcccttga cgttggagtc cacgttcttt aatagtggac tcttgttcca aactggaaca    8700
acactcaacc ctatctcggt ctattctttt gatttataag ggattttgcc gatttcggcc    8760
tattggttaa aaaatgagct gatttaacaa aaatttaacg cgaattttaa caaaatatta    8820
acgcttacaa tttccattcg ccattcaggc tgcgcaactg ttgggaaggg cgatcggtgc    8880
```

```
                                                    -continued
gggcctcttc gctattacgc cagctggcga aaggggatg tgctgcaagg cgattaagtt    8940
gggtaacgcc agggttttcc cagtcacgac gttgtaaaac gacggccagt gccaagctcc    9000
cgcggggatc gactcataaa atagtaacct tctaatgcgt atctattgac taccaaccat    9060
tagtgtggtt gcagaaggcg gaattctccc ttcttcgaat tcagcttgct tttcattttt    9120
ttattttcca ttttcagtt tttgtttgtg tcgaatttag ccagttgctt ctccaagatg    9180 aaaaaaccc ctgcgcagtt tctgtgctgc aagatcctaa tcgactttc cacccccac     9240 aaaagtaaat gttcttttgt tacattcgcg tgggtagcta gctccccgaa tcttcaaagg    9300
acttagggac tgcactacat cagagtgtgt tcacctggtt tgctgcctgg tttgaaagaa    9360
aagagcaggg aactcgcggg ttcccggcga ataatcatgc gatagtcctt tggccttcca    9420
agtcgcatgt agagtagaca acagacaggg agggcaggaa ggatctttca ctgagatcct    9480
gtatcttgtt gggtaagtcg gatgaaaggg gaatcgtatg agattggaga ggatgcggaa    9540
gaggtaacgc cttttgttaa cttgtttaat tattatgggg caggcgagag ggggaggaat    9600
gtatgtgtgt gaggcgggcg agacggagcc atccaggcca ggtagaaata gagaaagccg    9660
aatgttagac aatatggcag cgtagtagag taggtaggta ggcaagtact gctagcaaag    9720
aggagaaggg taagctcact cttcgcattc cacaccgtta gtgtgtcagt ttgaacaaaa    9780
aaacaatcat cataccaatt gatggactgt ggactggct ttggaacggc ttttcggact    9840
gcgattattc gtgaggaatc aaggtaggaa tttggtcata tttacggaca acagtgggtg    9900
attcccatat ggagtaggaa acgagatca tggtatcctc agatatgttg cggaattctg    9960
ttcaccgcaa agttcagggt gctctggtgg gtttcggttg gtctttgctt tgcttctccc    10020
ttgtcttgca tgttaataat agcctagcct gtgagccgaa acttagggta ggcttagtgt    10080
tggaacgtac atatgtatca cgttgacttg gtttaaccag gcgacctggt agccagccat    10140
acccacacac gttttttgta tcttcagtat agttgtgaaa agtgtagcgg aaatttgtgg    10200
tccgagcaac agcgtctttt tctagtagtg cggtcggtta cttggttgac attggtattt    10260
ggactttgtt gctacaccat tcactacttg aagtcgagtg tgaagggtat gatttctagt    10320
ggtgaacacc tttagttacg taatgttttc attgctgttt tacttgagat ttcgattgag    10380
aaaaaggtat ttaatagctc gaatcaatgt gagaacagag agaagatgtt cttccctaac    10440 tcgaaggta tatgaggctt gtgtttctta ggagaattat tattcttttg ttatgttgcg    10500
cttgtagttg aaaaggtga agagacaaaa gctggaattg tgagcggata acaagctcaa    10560
cacttgaaat ttaggaaaga gcagaatttg gcaaaaaaaa taaaaaaaaa ataaacacac    10620
atactcatcg ag                                                     10632

<210> SEQ ID NO 9
<211> LENGTH: 30
<212> TYPE: DNA
<213> ORGANISM: unknown
<220> FEATURE:
<223> OTHER INFORMATION: primer

<400> SEQUENCE: 9
ggagacauga attcaatgaa aatcgaagaa                                      30

<210> SEQ ID NO 10
<211> LENGTH: 30
<212> TYPE: DNA
<213> ORGANISM: unknown
<220> FEATURE:
<223> OTHER INFORMATION: primer
```

<400> SEQUENCE: 10
gggaaaguaa gcttaatcct tccctcgatc                                          30

<210> SEQ ID NO 11
<211> LENGTH: 49
<212> TYPE: DNA
<213> ORGANISM: unknown
<220> FEATURE:
<223> OTHER INFORMATION: primer

<400> SEQUENCE: 11
gactcatatg aaaatcgaag aaggtaaact ggtaatctgg attaacggc                     49

<210> SEQ ID NO 12
<211> LENGTH: 33
<212> TYPE: DNA
<213> ORGANISM: unknown
<220> FEATURE:
<223> OTHER INFORMATION: primer

<400> SEQUENCE: 12
atataagctt tcaccttccc tcgatcccga ggt                                      33

<210> SEQ ID NO 13
<211> LENGTH: 24
<212> TYPE: DNA
<213> ORGANISM: unknown
<220> FEATURE:
<223> OTHER INFORMATION: primer

<400> SEQUENCE: 13
cttcaagggt caaccatcca aacc                                                24

<210> SEQ ID NO 14
<211> LENGTH: 27
<212> TYPE: DNA
<213> ORGANISM: unknown
<220> FEATURE:
<223> OTHER INFORMATION: primer

<400> SEQUENCE: 14
aatacgcgga tctttcacca actcttc                                             27

<210> SEQ ID NO 15
<211> LENGTH: 27
<212> TYPE: DNA
<213> ORGANISM: unknown
<220> FEATURE:
<223> OTHER INFORMATION: primer

<400> SEQUENCE: 15
gaagagttgg tgaaagatcc gcgtatt                                             27

<210> SEQ ID NO 16
<211> LENGTH: 28
<212> TYPE: DNA
<213> ORGANISM: unknown
<220> FEATURE:
<223> OTHER INFORMATION: primer

<400> SEQUENCE: 16
ctgagaattc tgaaatcctt ccctcgat                                            28

<210> SEQ ID NO 17

```
<211> LENGTH: 24
<212> TYPE: DNA
<213> ORGANISM: unknown
<220> FEATURE:
<223> OTHER INFORMATION: primer

<400> SEQUENCE: 17
ccagaagtga cggcaacggt gatt                                          24

<210> SEQ ID NO 18
<211> LENGTH: 30
<212> TYPE: DNA
<213> ORGANISM: unknown
<220> FEATURE:
<223> OTHER INFORMATION: primer

<400> SEQUENCE: 18
aagtgcggcg acgatagtca tgccccgcgc                                    30

<210> SEQ ID NO 19
<211> LENGTH: 37
<212> TYPE: DNA
<213> ORGANISM: unknown
<220> FEATURE:
<223> OTHER INFORMATION: primer

<400> SEQUENCE: 19
gtgatttctt atgacaacta cgtcaccatc cttgatg                            37

<210> SEQ ID NO 20
<211> LENGTH: 30
<212> TYPE: DNA
<213> ORGANISM: unknown
<220> FEATURE:
<223> OTHER INFORMATION: primer

<400> SEQUENCE: 20
ttaaggatcc ttagtgcgcc tgatcccagt                                    30

<210> SEQ ID NO 21
<211> LENGTH: 25
<212> TYPE: DNA
<213> ORGANISM: unknown
<220> FEATURE:
<223> OTHER INFORMATION: primer

<400> SEQUENCE: 21
ccatagcata tgaaaatcga agaag                                         25

<210> SEQ ID NO 22
<211> LENGTH: 27
<212> TYPE: DNA
<213> ORGANISM: unknown
<220> FEATURE:
<223> OTHER INFORMATION: primer

<400> SEQUENCE: 22
cttgaatgca taaccccgt cagcagc                                        27

<210> SEQ ID NO 23
<211> LENGTH: 30
<212> TYPE: DNA
<213> ORGANISM: unknown
<220> FEATURE:
<223> OTHER INFORMATION: primer

<400> SEQUENCE: 23
```
ggttatgcat tcaagtatga aaacggcaag                                    30

<210> SEQ ID NO 24
<211> LENGTH: 42
<212> TYPE: DNA
<213> ORGANISM: unknown
<220> FEATURE:
<223> OTHER INFORMATION: primer

<400> SEQUENCE: 24
tatgcattca aatacggtga cattaaagac gtgggcgtgg at                      42

<210> SEQ ID NO 25
<211> LENGTH: 39
<212> TYPE: DNA
<213> ORGANISM: unknown
<220> FEATURE:
<223> OTHER INFORMATION: primer

<400> SEQUENCE: 25
gcggcgtttt ccgcagtggc ggcaatacgt ggatctttc                          39

<210> SEQ ID NO 26
<211> LENGTH: 39
<212> TYPE: DNA
<213> ORGANISM: unknown
<220> FEATURE:
<223> OTHER INFORMATION: primer

<400> SEQUENCE: 26
gcggaaaacg ccgcgaaagg tgaaatcatg ccgaacatc                          39

<210> SEQ ID NO 27
<211> LENGTH: 29
<212> TYPE: DNA
<213> ORGANISM: unknown
<220> FEATURE:
<223> OTHER INFORMATION: primer

<400> SEQUENCE: 27
ggatggttgg ttcgctaaac tgcatcgtc                                     29

<210> SEQ ID NO 28
<211> LENGTH: 29
<212> TYPE: DNA
<213> ORGANISM: unknown
<220> FEATURE:
<223> OTHER INFORMATION: primer

<400> SEQUENCE: 28
tattaatcat tcttctcata tacttcaaa                                     29

<210> SEQ ID NO 29
<211> LENGTH: 25
<212> TYPE: DNA
<213> ORGANISM: unknown
<220> FEATURE:
<223> OTHER INFORMATION: primer

<400> SEQUENCE: 29
ggatggtgaa ggtcggtgtg aacgg                                         25

<210> SEQ ID NO 30
<211> LENGTH: 28
<212> TYPE: DNA

```
<213> ORGANISM: unknown
<220> FEATURE:
<223> OTHER INFORMATION: primer

<400> SEQUENCE: 30
tattactcct tggaggccat gtaggcca                                    28

<210> SEQ ID NO 31
<211> LENGTH: 34
<212> TYPE: DNA
<213> ORGANISM: unknown
<220> FEATURE:
<223> OTHER INFORMATION: primer

<400> SEQUENCE: 31
gcccaagctt gccaccatga aaatcgaaga aggt                             34

<210> SEQ ID NO 32
<211> LENGTH: 45
<212> TYPE: DNA
<213> ORGANISM: unknown
<220> FEATURE:
<223> OTHER INFORMATION: primer

<400> SEQUENCE: 32
gcgctcgagc ttgtcatcgt catccgagct cgaattagtc tgcgc                 45

<210> SEQ ID NO 33
<211> LENGTH: 30
<212> TYPE: DNA
<213> ORGANISM: unknown
<220> FEATURE:
<223> OTHER INFORMATION: primer

<400> SEQUENCE: 33
gcgctcgaga attccgcatt cggtagtatg                                  30

<210> SEQ ID NO 34
<211> LENGTH: 43
<212> TYPE: DNA
<213> ORGANISM: unknown
<220> FEATURE:
<223> OTHER INFORMATION: primer

<400> SEQUENCE: 34
ataagaatgc ggccgctcac gacgttgtaa aacgacggcc agt                   43
```

What is claimed is:

1. A variant MBP having a modified amino acid sequence as compared to SEQ ID NO:2, wherein amino acid residue S146 and/or A313 is mutated.

2. A variant MBP comprising SEQ ID NO:4 or SEQ ID NO:6.

3. A fusion protein comprising the variant MBP of claim 1 or 2 and a target protein.

4. An isolated DNA encoding a variant MBP of claim 1 or 2.

5. A method for increasing the solubility of a protein, comprising:
   fusing to the variant MBP of claim 1 or 2, a target protein, thereby increasing the solubility of the target protein compared to the target protein in the absence of the variant MBP.

6. The method according to claim 5, wherein fusing the protein to the variant MBP comprises expressing a DNA encoding the variant MBP fused in frame to a DNA encoding the protein in a host cell.

7. A protein purification method, comprising: permitting a fusion protein comprising a variant MBP according to claim 1 or 2 and a target protein to bind to a matrix; and eluting the fusion protein from the matrix in a selected buffer to obtain the purified protein.

* * * * *

UNITED STATES PATENT AND TRADEMARK OFFICE
CERTIFICATE OF CORRECTION

PATENT NO.       : 7,825,218 B2
APPLICATION NO.  : 12/297105
DATED            : November 2, 2010
INVENTOR(S)      : Paul Riggs et al.

It is certified that error appears in the above-identified patent and that said Letters Patent is hereby corrected as shown below:

The Sequence Listing starting at Col. 13, Line 33 and ending at Col. 46, Line 49 should be deleted and replaced with the attached Sequence Listing.

| Error code | Error Description |
|---|---|
| W 213 | Artificial or Unknown found in <213> in SEQ ID (1) |
| W 213 | Artificial or Unknown found in <213> in SEQ ID (2) |
| W 213 | Artificial or Unknown found in <213> in SEQ ID (3) |
| W 213 | Artificial or Unknown found in <213> in SEQ ID (4) |
| W 213 | Artificial or Unknown found in <213> in SEQ ID (5) |
| W 213 | Artificial or Unknown found in <213> in SEQ ID (6) |
| W 213 | Artificial or Unknown found in <213> in SEQ ID (7) |
| W 213 | Artificial or Unknown found in <213> in SEQ ID (8) |
| W 213 | Artificial or Unknown found in <213> in SEQ ID (9) |
| W 213 | Artificial or Unknown found in <213> in SEQ ID (10) |
| W 213 | Artificial or Unknown found in <213> in SEQ ID (11) |
| W 213 | Artificial or Unknown found in <213> in SEQ ID (12) |
| W 213 | Artificial or Unknown found in <213> in SEQ ID (13) |
| W 213 | Artificial or Unknown found in <213> in SEQ ID (14) |

Signed and Sealed this
Twenty-ninth Day of November, 2011

David J. Kappos
*Director of the United States Patent and Trademark Office*

| Error code | Error Description |
|---|---|
| W 213 | Artificial or Unknown found in <213> in SEQ ID (15) |
| W 213 | Artificial or Unknown found in <213> in SEQ ID (16) |
| W 213 | Artificial or Unknown found in <213> in SEQ ID (17) |
| W 213 | Artificial or Unknown found in <213> in SEQ ID (18) |
| W 213 | Artificial or Unknown found in <213> in SEQ ID (19) |
| W 213 | Artificial or Unknown found in <213> in SEQ ID (20) |
| | This error has occurred more than 20 times, will not be displayed |

```
                         SEQUENCE LISTING

<110>   New England Biolabs, Inc.
            Riggs, Paul
            Hsieh, Pei-chung
            Walker, Iris
            Colussi, Paul
            Ganatra, Mehul
            Taron, Christopher <120>   Expression and Purification of a Target Protein Fused to a
            Modified Maltose-Binding Protein

<130>   NEB-274-PUS

<140>   12297105
    <141>   2011-10-25

<150>   60/792,133
    <151>   2006-04-14

<150>   PCT/US07/09100
    <151>   2007-04-14

<160>   34

<170>   PatentIn version 3.5

<210>   1
    <211>   1188
    <212>   DNA
    <213>   artificial

<220>
    <223>   DNA sequence encoding wild-type maltose-binding protein from
            pMAL-c2X <400>   1
    gcacttcacc aacaaggacc atagcatatg aaaatcgaag aaggtaaaact ggtaatctgg      60 attaacggcg ataaaggcta taacggtctc gctgaagtcg gtaagaaatt cgagaaagat     120
accggaatta aagtcaccgt tgagcatccg ataaactgg aagagaaatt cccacaggtt      180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta taacaaagat ctgctgccga acccgccaaa aacctgggaa     420
gagatcccgg cgctggataa agaactgaaa gcgaaggta agagcgcgct gatgttcaac     480
ctgcaagaac cgtacttcac ctggccgctg attgctgctg acgggggtta tgcgttcaag     540
```

```
tatgaaaacg gcaagtacga cattaaagac gtgggcgtgg ataacgctgg cgcgaaagcg        600
ggtctgacct tcctggttga cctgattaaa aacaaacaca tgaatgcaga caccgattac        660
tccatcgcag aagctgcctt taataaaggc gaaacagcga tgaccatcaa cggcccgtgg        720
gcatggtcca acatcgacac cagcaaagtg aattatggtg taacggtact gccgaccttc        780
aagggtcaac catccaaacc gttcgttggc gtgctgagcg caggtattaa cgccgccagt        840
ccgaacaaag agctggcaaa agagttcctc gaaaactatc tgctgactga tgaaggtctg        900
gaagcggtta ataaagacaa accgctgggt gccgtagcgc tgaagtctta cgaggaagag        960
ttggcgaaag atccacgtat tgccgccact atggaaaacg cccagaaagg tgaaatcatg       1020
ccgaacatcc cgcagatgtc cgctttctgg tatgccgtgc gtactgcggt gatcaacgcc       1080
gccagcggtc gtcagactgt cgatgaagcc ctgaaagacg cgcagactaa ttcgagctcg       1140
aacaacaaca acaataacaa taacaacaac ctcgggatcg agggaagg                   1188
```

<210> 2
<211> 387
<212> PRT
<213> artificial

<220>
<223> wild-type maltose-binding protein from pMAL-c2X

<400> 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

CERTIFICATE OF CORRECTION (continued)
U.S. Pat. No. 7,825,218 B2

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
```

```
                     325                  330                  335

Met Ser Ala Phe Trp Tyr Ala Val Arg Thr Ala Val Ile Asn Ala Ala
                340                  345                  350

Ser Gly Arg Gln Thr Val Asp Glu Ala Leu Lys Asp Ala Gln Thr Asn
                355                  360                  365

Ser Ser Ser Asn Asn Asn Asn Asn Asn Asn Asn Asn Leu Gly Ile
                370                  375                  380

Glu Gly Arg
    385

<210>  3
<211>  1188
<212>  DNA
<213>  unknown

<220>
<223>  DNA sequence encoding the maltose binding protein mutant A9

<400>  3
gcacttcacc aacaaggacc atagcatatg aaaatcgaag aaggtaaact ggtaatctgg        60
attaacggcg ataaaggcta tagcggtctc gctgaagtcg gtaagaaatt cgagaaagat       120
accggaatta aagtcaccgt tgagcatccg gataaactgg aagagaaatt cccacaggtt       180
gcggcaactg gcgatggccc tgacattatc ttctgggcac acgaccgctt tggtggctac       240
gctcaatctg gcctgttggc tgaaatcacc ccggacaaag cgttccagga caagctgtat       300
ccgtttacct gggatgccgt acgttacaac ggcaagctga ttgcttaccc gatcgctgtt       360
gaagcgttat cgctgattta taacaaagat ctgctgccga cccgccaaa aacctgggaa        420 gagatcccgg cgctggataa agaactgaaa gcgaaggta gagcgcgct gatgttcaac         480 ctgcaagaac cgtacttcac ctggccgctg attgctgctg acgggggtta tgcgttcaag       540
tatgaaaacg gcaagtacga cattaaagac gtgggcgtgg ataacgctgg cgcgaaagcg       600
ggtctgacct tcctggttga cctgattaag aacaaacaca tgaatgcaga caccgattac       660
tccatcgcag aagctgcctt taataaaggc gaaacagcga tgaccatcaa cggcccgtgg       720
gcatggtcca acatcgacac cagcaaagtg aattatggtg taacggtact gccgaccttc       780
aagggtcaac catccaaacc gttcgttggc gtgctgagcg caggtattaa cgccgccagt       840
ccgaacaaag agctggcaaa agagttcctc gaaaactatc tgctgactga tgaaggtctg       900
```

```
gaagcggtta ataaagacga accgctgggt gccgtagcgc tgaagtctta cgaggaagag    960
ttggtgaaag atccacgtat tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctcg   1140
aacaacaaca acaataacaa taacaacaac ctcgggatcg agggaagg              1188
```

<210> 4
<211> 387
<212> PRT
<213> unknown

<220>
<223> maltose binding protein mutant A9

<400> 4

```
Met Lys Ile Glu Glu Gly Lys Leu Val Ile Trp Ile Asn Gly Asp Lys
1               5                   10                  15

Gly Tyr Ser Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140
```

```
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Glu Pro Leu Gly Ala Val Ala
            290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365
```

```
Ser Ser Ser Asn Asn Asn Asn Asn Asn Asn Asn Asn Leu Gly Ile
    370                 375                 380

Glu Gly Arg
385

<210> 5
<211> 1188
<212> DNA
<213> unknown

<220>
<223> DNA sequence encoding the maltose binding protein mutant G8-1

<400> 5
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga cccgccaaa aacctgggaa      420 gagatcccgg cgctggataa agaactgaaa gcgaaggta agaccgcgct gatgttcaac      480
ctgcaagaac cgtacttcac ctggccgctg attgctgctg acggggcta tgcgttcaag     540 tatgaaaacg gcaagtacga cattaaagac gtgggcgtgg ataacgctgg cgcgaaagcg     600
ggtctgacct tcctggttga cctgattaaa aacaaacaca tgaatgcaga caccgattac     660
tccatcgcag aagctgcctt taataaaggc gaaacagcga tgaccatcaa cggcccgtgg     720
gcatggtcca acatcgacac cagcaaagtg aattatggtg taacggtact gccgaccttc     780
aagggtcaac catccaaacc gttcgttggc gtgctgagcg caggtattaa cgccgccagt     840
ccgaacaaag agctggcaaa agagttcctc gaaaactatc tgctgactga tgaaggtctg     900
gaagcggtta taaagacaa accgctgggt gccgtagcgc tgaagtctta cgaggaagag     960
ttggcgaaag atccacgtat tgccgccact atggaaaacg cccagaaagg tgaaatcatg    1020
ccgaacatcc cgcagatgtc cgctttctgg tatgccgtgc gtactgcggt gatcaacgcc    1080
gccagcggtc gtcagactgt cgatgaagcc ctgaaagacg cgcagactaa ttcgagctcg    1140
aacaacaaca acaataacaa taacaacaac ctcgggatcg agggaagg                1188
```

```
<210>  6
<211>  387
<212>  PRT
<213>  unknown

<220>
<223>  maltose binding protein mutant G8-1

<400>  6
```

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Thr Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

```
Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
        370                 375                 380

Glu Gly Arg
385

<210>  7
<211>  6835
<212>  DNA
```

```
<213>  unknown

<220>
<223>  pMB50

<400>  7
ccgacaccat cgaatggtgc aaaacctttc gcggtatggc atgatagcgc ccggaagaga         60
gtcaattcag ggtggtgaat gtgaaaccag taacgttata cgatgtcgca gagtatgccg        120
gtgtctctta tcagaccgtt tcccgcgtgg tgaaccaggc cagccacgtt tctgcgaaaa        180
cgcgggaaaa agtggaagcg gcgatggcgg agctgaatta cattcccaac cgcgtggcac        240
aacaactggc gggcaaacag tcgttgctga ttggcgttgc cacctccagt ctggccctgc        300
acgcgccgtc gcaaattgtc gcggcgatta atctcgcgc cgatcaactg ggtgccagcg         360
tggtggtgtc gatggtagaa cgaagcggcg tcgaagcctg taaagcggcg gtgcacaatc        420
ttctcgcgca acgcgtcagt gggctgatca ttaactatcc gctggatgac caggatgcca        480
ttgctgtgga agctgcctgc actaatgttc cggcgttatt tcttgatgtc tctgaccaga        540
cacccatcaa cagtattatt ttctcccatg aagacggtac gcgactgggc gtggagcatc        600
tggtcgcatt gggtcaccag caaatcgcgc tgttagcggg cccattaagt tctgtctcgg        660
cgcgtctgcg tctggctggc tggcataaat atctcactcg caatcaaatt cagccgatag        720
cggaacggga aggcgactgg agtgccatgt ccggttttca acaaaccatg caaatgctga        780
atgagggcat cgttcccact gcgatgctgg ttgccaacga tcagatggcg ctgggcgcaa        840
tgcgcgccat taccgagtcc gggctgcgcg ttggtgcgga tatctcggta gtgggatacg        900
acgataccga agacagctca tgttatatcc cgccgttaac caccatcaaa caggattttc        960
gcctgctggg gcaaaccagc gtggaccgct tgctgcaact ctctcagggc caggcggtga       1020
agggcaatca gctgttgccc gtctcactgg tgaaaagaaa aaccaccctg gcgcccaata       1080
cgcaaaccgc ctctccccgc gcgttggccg attcattaat gcagctggca cgacaggttt       1140
cccgactgga aagcgggcag tgagcgcaac gcaattaatg tgagttagct cactcattag       1200
gcacaattct catgtttgac agcttatcat cgactgcacg gtgcaccaat gcttctggcg       1260
tcaggcagcc atcggaagct gtggtatggc tgtgcaggtc gtaaatcact gcataattcg       1320
tgtcgctcaa ggcgcactcc cgttctggat aatgttttt gcgccgacat cataacggtt       1380
ctggcaaata ttctgaaatg agctgttgac aattaatcat cggctcgtat aatgtgtgga       1440
attgtgagcg gataacaatt tcacacagga aacagccagt ccgtttaggt gttttcacga
```